(12) United States Patent
Boudon et al.

(10) Patent No.: US 10,550,097 B2
(45) Date of Patent: Feb. 4, 2020

(54) SELECTIVE 11-BETA-HYDROXYSTEROID DEHYDROGENASE TYPE 1 INHIBITORS

(71) Applicant: DSM IP ASSETS B.V., Heerlen (NL)

(72) Inventors: Stéphanie Boudon, Kaiseraugst (CH); Piero Geotti-Bianchini, Kaiseraugst (CH); Marc Heidl, Kaiseraugst (CH); Eileen Jackson, Kaiseraugst (CH); Alexander Schlifke-Poschalko, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/745,754

(22) PCT Filed: Jul. 7, 2016

(86) PCT No.: PCT/EP2016/066182
§ 371 (c)(1),
(2) Date: Jan. 18, 2018

(87) PCT Pub. No.: WO2017/012890
PCT Pub. Date: Jan. 26, 2017

(65) Prior Publication Data
US 2018/0208576 A1    Jul. 26, 2018

(30) Foreign Application Priority Data

Jul. 23, 2015 (EP) .................... 15178034

(51) Int. Cl.
| | | |
|---|---|---|
| C07D 401/10 | (2006.01) | |
| A61K 8/49 | (2006.01) | |
| A61Q 19/08 | (2006.01) | |
| C07D 223/04 | (2006.01) | |
| C07D 265/30 | (2006.01) | |
| C07D 211/16 | (2006.01) | |

(52) U.S. Cl.
CPC .......... *C07D 401/10* (2013.01); *A61K 8/4926* (2013.01); *A61Q 19/08* (2013.01); *C07D 211/16* (2013.01); *C07D 223/04* (2013.01); *C07D 265/30* (2013.01)

(58) Field of Classification Search
None
See application file for complete search history.

(56) References Cited

U.S. PATENT DOCUMENTS

2009/0124598 A1  5/2009 Andersen et al.
2015/0191451 A1  7/2015 Boiteau et al.

FOREIGN PATENT DOCUMENTS

| KR | 20140071892 | * | 6/2014 | ........... A61K 31/437 |
| WO | 2014/088129 | | 6/2014 | |

OTHER PUBLICATIONS

International Search Report for PCT/EP2016/066182 dated Oct. 7, 2016, 5 pages.
Written Opinion of the ISA, for PCT/EP2016/066182 dated Oct. 7, 2016, 9 pages.
Database Registry [Online], Chemical Abstracts Service, Mar. 30, 2012 & Database Registry [Online], Chemical Abstracts Service, Jan. 1, 2015—Catalog Name: Aurora Screening Library, 1 page.
Tiganescu et al., "11 [beta]-Hydroxysteroid dehydrogenase blockade prevents age-induced skin structure and function defects", Journal of Clinical Investigation, vol. 123, No. 7, Jul. 1, 2013, pp. 3051-3060.
Lauwagie et al., "Expeditious synthesis of 2-aryl substituted imidazolines and imidazoles", Heterocycles: An International Journal for Reviews and Communications in Heterocyclic Chemistry, vol. 68, Jan. 1, 2006, pp. 1149-1162.
Sezen et al., "Selective Catalytic Arylation of N-Phenylpyrrolidine: sp 3 C-H Bond Functionalization in the Absence of a Directing Group", Journal of the American Chemical Society, vol. 127, No. 15, Apr. 1, 2005, pp. 5284-5285 and Sezen et al., Supporting information—"Selective Catalytic Arylation of N-Phenylpyrrolidine: sp 3 C-H Bond Functionalization in the Absence of a Directing Group Supporting Information Part I: Arylation of Other Substrates", Journal of the American Chemical Society, Apr. 1, 2005, pp. S1-S32.
Wang et al., "A general ligand design for gold catalysis allowing ligand-directed anti-nucleophilic attack of alkynes", Nature Communications, vol. 5, Apr. 7, 2014, pp. 4470/1-4470/8.
Flyren et al., "Piperidine amides as 11beta-hydroxysteroid dehydrogenase type 1 inhibitors", Bioorganic & Medicinal Chemistry Letters, vol. 17, No. 12, Jun. 15, 2007, pp. 3421-3425.
Zhang et al., "4-(Phenylsulfonamidomethyl) benzamides as potent and selective inhibitors of the 11[beta]-hydroxysteroid dehydrogenase type 1 with efficacy in diabetic ob/ob mice", Bioorganic & Medicinal Chemistry Letters, vol. 19, No. 15, May 15, 2009, pp. 4455-4458.
Burk et al., "A Versatile Tandem Catalysis Procedure for the Preparation of Novel Amino Acids and Peptides", J. Am. Chem. Soc., vol. 116, 1994, pp. 10847-10848.
Venkatraj et al., Synthesis and evaluation of non-basic inhibitors of urokinase-type plasminogen activator (uPA), Bioorganic & Medicinal Chemistry, vol. 20, 2012, pp. 1557-1558.
Korolev et al., "Pd-EDTA as an efficient catalyst for Suzuki-Miyaura reactions in water", Tetrahedron Letters, vol. 46, 2005, pp. 5751-5754.

* cited by examiner

*Primary Examiner* — Aradhana Sasan
(74) *Attorney, Agent, or Firm* — Nixon & Vanderhye P.C.

(57) ABSTRACT

The present invention relates to novel selective 11-beta-hydroxysteroid dehydrogenase type 1 (11β-HSD1) inhibitors and the use thereof to prevent age-induced skin structure and function defects.

21 Claims, No Drawings

SELECTIVE 11-BETA-HYDROXYSTEROID DEHYDROGENASE TYPE 1 INHIBITORS

This application is the U.S. national phase of International Application No. PCT/EP2016/066182 filed Jul. 7, 2016 which designated the U.S. and claims priority to EP Patent Application No. 15178034.3 filed Jul. 23, 2015, the entire contents of each of which are hereby incorporated by reference.

The present invention relates to novel selective 11-beta-hydroxysteroid dehydrogenase type 1 (11β-HSD1) inhibitors and the use thereof to prevent age-induced skin structure and function defects.

Glucocorticoid (GC) excess adversely affects skin integrity, inducing thinning and impaired wound healing. Aged skin, such as in particular photo-exposed skin, shares a similar phenotype. Elevated 11β-HSD1 activity in aging skin leads to increased local GC generation, which may account for age-associated impairments in dermal integrity such as dermal and epidermal thinning, increased fragility of the skin, decrease of dermal collagen and increased trans-epidermal water loss. Furthermore, increased local GC concentration leads to poor wound healing [Tiganescu et al, J Clin Invest. 2013; 123(7):3051-3060].

Thus, the topical administration of an effective amount of an 11β-HSD1 inhibitor is useful in the treatment of age-associated impairments in dermal integrity and wound healing. Long-term treatment with an 11β-HSD1 inhibitor is also useful in delaying the onset of aging.

Surprisingly it has been found that compounds of formula (I)

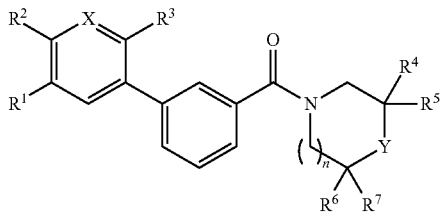

wherein X is CH or N,
Y is CHR$^8$ or O,
n is 0, 1 or 2,
R$^1$, R$^2$ and R$^3$ are independently of each other selected from the group consisting of H, OH, a halogen atom, a carbamoyl group and C$_1$-C$_6$alkyl group, and
R$^4$, R$^5$, R$^6$, R$^7$ and, R$^8$ are independently of each other selected from H or a C$_1$-C$_6$alkyl group are highly efficient 11β-HSD1 inhibitors, which are soluble in cosmetic oils and thus particularly suitable for the incorporation into cosmetic compositions for the treatment of age-associated impairments in dermal integrity and wound healing.

Thus, in a first aspect, the present invention relates to cosmetic compositions comprising a compound of formula (I)

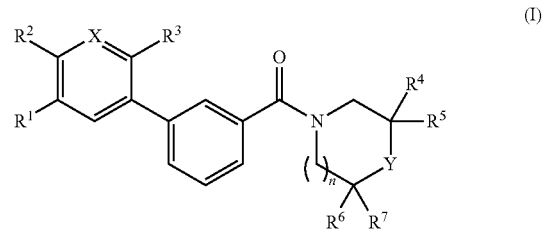

wherein X is CH or N,
Y is CHR$^8$ or O,
n is 0, 1 or 2, preferably 1 or 2,
R$^1$, R$^2$ and R$^3$ are independently of each other selected from the group consisting of H, OH, a halogen atom, a carbamoyl group and C$_1$-C$_6$alkyl group, and
R$^4$, R$^5$, R$^6$, R$^7$ and R$^8$ are independently of each other H or a C$_1$-C$_6$alkyl group, and a cosmetically acceptable carrier.

Some of the compounds are also novel. Thus, the invention also relates to compounds of formula (I) which are compounds of formula (Ia)

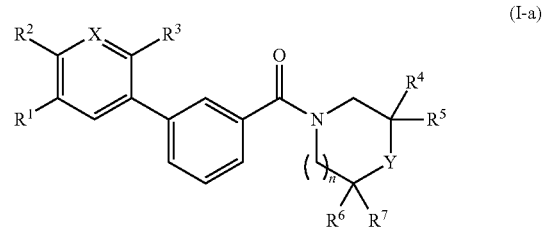

wherein X is CH or N,
Y is CHR$^8$ or O,
n is 1 or 2,
R$^1$, R$^2$ and R$^3$ are independently of each other selected from the group consisting of H, OH, a halogen atom, a carbamoyl group and a C$_1$-C$_6$alkyl group, and
R$^4$, R$^5$, R$^6$, R$^7$ and R$^8$ are independently of each other H or a C$_1$-C$_6$alkyl group,
with the proviso that if
(i) n is 1 and Y is CHR$^8$, then at least one of R$^4$, R$^5$ or R$^8$ is a C$_{1-6}$alkyl group; or
(ii) n is 2, Y is CHR$^8$, X is CH and R$^1$, R$^3$, R$^4$, R$^5$, R$^6$, R$^7$ and R$^8$ are H, then R$^2$ is not F; or
(iii) n is 1 and Y is O, then R$^2$ and at least one of R$^4$ or R$^5$ are a C$_1$-C$_6$alkyl group.

In all embodiments of the present invention particularly advantageous compounds according to formula (I) contain only one residue selected from the group consisting of OH, a halogen atom and a carbamoyl group (C=ONH$_2$).

Examples of C$_1$-C$_6$alkyl groups according to the present invention are unbranched C$_1$-C$_6$alkyl or branched C$_3$-C$_6$alkyl groups such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2- methylpropyl groups. In all embodiments of the present invention particularly preferred $C_1$-$C_6$alkyl groups are unbranched $C_1$-$C_3$alkyl groups, more preferably $C_1$-$C_2$alkyl groups, most preferably methyl groups.

Suitable halogen atoms encompass F, Cl, Br and I. Preferably in all embodiments of the present invention the halogen atoms are either F or Cl.

It is well understood, that the present invention encompasses (if applicable) the compounds of formula (I) as optically pure isomers such as e.g. as pure enantiomers or as mixture of different isomers such as e.g. as racemates.

Particularly preferred compounds in all embodiments according to the present invention are compounds of formula (I), which are compounds of formula (II),

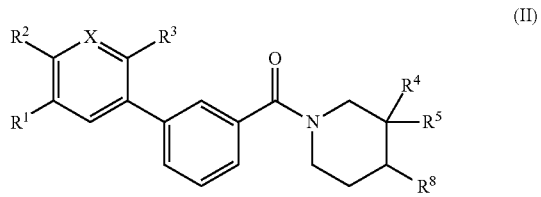

wherein X is CH or N,
$R^1$, $R^2$ and $R^3$ are independently of each other selected from the group consisting of H, OH, a halogen atom, a carbamoyl group and a $C_1$-$C_6$alkyl group, and
$R^4$, $R^5$ and $R^8$ are independently of each other H or a $C_1$-$C_6$alkyl group,
with the proviso that at least one of $R^4$, $R^5$ and $R^8$ is a $C_{1-6}$alkyl group.

Particular advantageous compounds of formula (II) are the ones wherein X is CH or N,
$R^1$ and $R^2$ are selected independently of each other from the group consisting of H, OH, F, Cl, a carbamoyl group and a methyl group,
$R^3$ is H or Cl,
$R^4$, $R^5$ and $R^{85}$ are independently of each other H or a methyl group,
with the proviso that at least one of $R^4$, $R^5$ and $R^8$ is a methyl group and only one residue selected from the group consisting of OH, F, Cl and a carbamoyl group is present in the compound of formula (II).

Even more advantageous are compounds of formula (II) wherein X is CH or N,
$R^1$ and $R^2$ are selected independently of each other from the group consisting of H, OH, F, Cl, a carbamoyl group and a methyl group,
$R^3$ is H or Cl, and
$R^8$ is H when both of $R^4$ and $R^5$ are a methyl group, or
$R^8$ is a methyl group when both of $R^4$ and $R^5$ are H,
with the proviso that only one residue selected from the group consisting of OH, F, Cl and a carbamoyl group is present in the compound of formula (II).

Most preferred compounds of formula (II) are outlined in table 1.

TABLE 1

| Structure | Compound of formula (II) with | Name |
|---|---|---|
| | (II-a) $R^1$, $R^3$, $R^4$ & $R^5$ = H<br>$R^2$ & $R^8$ = $CH_3$<br>X = N | (4-methylpiperidin-1-yl)(3-(6-methylpyridin-3-yl)phenyl)methanone |
| | (II-b) $R^1$, $R^3$, $R^4$ & $R^5$ = H<br>$R^2$ = OH<br>$R^8$ = $CH_3$<br>X = CH | (4'-hydroxy-[1,1'-biphenyl]-3-yl)(4-methylpiperidin-1-yl)methanone |
| | (II-c) $R^1$, $R^3$, $R^4$ & $R^5$ = H<br>$R^2$ = F<br>$R^8$ = $CH_3$<br>X = CH | (4'-fluoro-[1,1'-biphenyl]-3-yl)(4-methylpiperidin-1-yl)methanone |
| | (II-d) $R^3$, $R^4$, & $R^5$ = H<br>$R^1$ = F<br>$R^2$ & $R^8$ = $CH_3$<br>X = CH | (3'-fluoro-4'-methyl-[1,1'-biphenyl]-3-yl)(4-methylpiperidin-1-yl)methanone |

TABLE 1-continued

| Structure | Compound of formula (II) with | Name |
|---|---|---|
| (II-e) | $R^1, R^2, R^4$ & $R^5$ = H<br>$R^3$ = Cl<br>$R^8$ = $CH_3$<br>X = CH | (2'-chloro-[1,1'-biphenyl]-3-yl)(4-methylpiperidin-1-yl)methanone |
| (II-f) | $R^1, R^3, R^4$ & $R^5$ = H<br>$R^2$ & $R^8$ = $CH_3$<br>X = CH | (4'-methyl-[1,1'-biphenyl]-3-yl)(4-methylpiperidin-1-yl)methanone |
| (II-g) | $R^1, R^3, R^4$ & $R^5$ = H<br>$R^2$ = Cl<br>$R^8$ = $CH_3$<br>X = CH | (4'-chloro-[1,1'-biphenyl]-3-yl)(4-methylpiperidin-1-yl)methanone |
| (II-h) | $R^3$ & $R^8$ = H<br>$R^1$ = F<br>$R^2, R^4$ & $R^5$ = $CH_3$<br>X = CH | (3,3-dimethylpiperidin-1-yl)(3'-fluoro-4'-methyl-[1,1'-biphenyl]-3-yl)methanone |
| (II-i) | $R^1, R^3, R^4$ & $R^5$ = H<br>$R^2$ = 'C=ONH$_2$'<br>$R^8$ = $CH_3$<br>X = CH | 3'-(4-methylpiperidine-1-carbonyl)-[1,1'-biphenyl]-4-carboxamide |
| (II-j) | $R^2, R^3, R^4$ & $R^5$ = H<br>$R^1$ = OH<br>$R^8$ = $CH_3$<br>X = CH | (3'-hydroxy-[1,1'-biphenyl]-3-yl)(4-methylpiperidin-1-yl)methanone |
| (II-k) | $R^2, R^3, R^4$ & $R^5$ = H<br>$R^1$ = 'C=ONH$_2$'<br>$R^8$ = $CH_3$<br>X = CH | 3'-(4-methylpiperidine-1-carbonyl)-[1,1'-biphenyl]-3-carboxamide |

Further particularly preferred compounds in all embodiments according to the present invention are compounds of formula (I), which are compounds of formula (III)

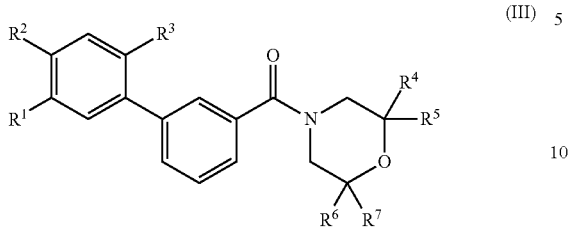

(III)

wherein $R^1$ and $R^3$ are independently of each other selected from the group consisting
of H, OH, a halogen atom such as preferably F and a $C_1$-$C_6$alkyl group,
$R^2$ is a $C_1$-$C_6$alkyl group, and
$R^4$, $R^5$, $R^6$ and $R^7$ are independently of each other H or a $C_1$-$C_6$alkyl group, with the proviso that at least one of $R^4$ or $R^5$ is a $C_1$-$C_6$alkyl group.

Particular advantageous compounds of formula (III) are the ones
wherein $R^1$ is selected from the group consisting of H, F and a methyl group,
$R^2$ is a methyl group,
$R^3$ is H, and
$R^4$, $R^5$, $R^6$ and $R^7$ are independently of each other H or a methyl group, with the proviso that at least one of $R^4$ or $R^5$ is a methyl group.

It is furthermore particularly advantageous if
(i) $R^4$ and $R^5$ are a methyl group when $R^6$ and $R^7$ are H, or
(ii) $R^4$ and $R^6$ are a methyl group when $R^5$ and $R^7$ are H.

Most preferred compounds of formula (III) are outlined in table 2.

Additional particularly preferred compounds in all embodiments according to the present invention are compounds of formula (IV),

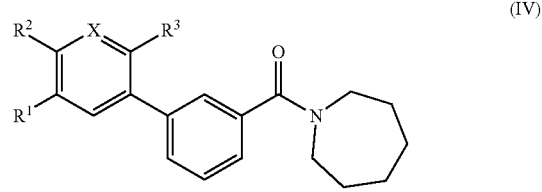

(IV)

wherein X is CH or N
$R^1$, $R^2$ and $R^3$ are independently of each other selected from the group consisting of H, OH, a halogen atom and a $C_1$-$C_6$alkyl group,
with the proviso that if X is CH and $R^1$ and $R^3$ are H, then $R^2$ is not a F atom.

Particular advantageous compounds of formula (IV) are the ones wherein $R^1$ and $R^2$ are selected from the group consisting of H, OH, a halogen atom
and a $C_1$-$C_6$alkyl group, preferably from the group consisting of H, OH, F, Cl and a methyl group, and
$R^3$ is H
with the proviso that if X is CH and $R^1$ is H, then $R^2$ is not a F atom.

Even more advantageous compounds of formula (IV) are the ones
wherein X is CH or N
$R^1$ is selected from the group consisting of H, F and a methyl group,
$R^2$ is selected from the group consisting of H, OH, F, Cl and methyl group, and
$R^3$ is H

TABLE 2

| Structure | Compound of formula(III) with | Name |
|---|---|---|
| | (III-a) $R^3$, $R^6$ & $R^7$ = H<br>$R^1$ = F<br>$R^2$, $R^4$ & $R^5$ = $CH_3$ | (2,2-dimethylmorpholino)(3'-fluoro-4'-methyl-[1,1'-biphenyl]-3-yl)methanone |
| | (III-b) $R^3$, $R^5$ & $R^7$ = H<br>$R^1$ = F<br>$R^2$, $R^4$ & $R^6$ = $CH_3$ | (2,6-dimethylmorpholino)(3'-fluoro-4'-methyl-[1,1'-biphenyl]-3-yl)methanone |
| | (III-c) $R^1$, $R^3$ $R^5$ & $R^7$ = H<br>$R^2$, $R^4$, $R^6$ = $CH_3$ | (2,6-dimethylmorpholino)(4'-methyl-[1,1'-biphenyl]-3-yl)methanone | with the proviso that if X is CH and $R^1$ is H, then $R^2$ is not a F atom.

Most preferred compounds of formula (IV) are outlined in table 3.

to prevent (photo)age-induced skin structure and function defects such as skin thinning and wrinkle formation.

Thus, the invention also relates to a method to smoothen wrinkles and fine lines and/or to decrease their volume and

TABLE 3

| Structure | Compound of formula (IV) with | Name |
|---|---|---|
| (IV-a) | $R^3$ = H<br>$R^2$ = $CH_3$<br>$R^1$ = F<br>X = CH | azepan-1-yl(3'-fluoro-4'-methyl-[1,1'-biphenyl]-3-yl)methanone |
| (IV-b) | $R^1$ & $R^3$ = H<br>$R^2$ = Cl<br>X = CH | azepan-1-yl(4'-chloro-[1,1'-biphenyl]-3-yl)methanone |
| (IV-c) | $R^1$ & $R^3$ = H<br>$R^2$ = $CH_3$<br>X = CH | azepan-1-yl(4'-methyl-[1,1'-biphenyl]-3-yl)methanone |
| (IV-d) | $R^1$ & $R^3$ = H<br>$R^2$ = OH<br>X = CH | azepan-1-yl(4'-hydroxy-[1,1'-biphenyl]-3-yl)methanone |
| (IV-e) | $R^1$ & $R^3$ = H<br>$R^2$ = $CH_3$<br>X = N | azepan-1-yl(3-(6-methylpyridin-3-yl)phenyl)methanone |
| (IV-f) | $R^1$, $R^2$ & $R^3$ = H<br>X = CH | [1,1'-biphenyl]-3-yl(azepan-1-yl)methanone |
| (IV-g) | $R^3$ = H<br>$R^1$ & $R^2$ = $CH_3$<br>X = CH | azepan-1-yl(3',4'-dimethyl-[1,1'-biphenyl]-3-yl)methanone |

In yet another embodiment the present invention relates to the use of a compound of formula (I) with all the definitions and preferences as given herein as 11β-HSD1 inhibitor, in particular for the treatment of age-associated impairments in dermal integrity and wound healing and the symptoms associated herewith such as wrinkles and fine lines. Furthermore, the compounds of formula (I) are particularly suited depth, said method comprising the step of applying a cosmetic composition according to the present invention with all the definitions and preferences given herein to the affected area.

The term 'cosmetic composition' refers to compositions which are used to treat, care for or improve the appearance of the skin and/or the scalp. Particular advantageous cosmetic compositions are skin care compositions.

The cosmetic compositions according to the invention are preferably intended for topical application, which is to be understood as the external application to keratinous substances, such as in particular the skin.

The term 'cosmetically acceptable carrier' as used herein refers to a physiologically acceptable medium which is compatible with keratinous substances. Suitable carriers are well known in the art and are selected based on the end-use application. Preferably, the carriers of the present invention are suitable for application to skin (e.g., sunscreens, creams, milks, lotions, masks, serums, hydrodispersions, foundations, creams, creamgels, or gels etc.). Such carriers are well-known to one of ordinary skill in the art, and can include one or more compatible liquid or solid filler diluent, excipient, additive or vehicle which are suitable for application to skin. The exact amount of carrier will depend upon the level of the compound of formula (I) and any other optional ingredients that one of ordinary skill in the art would classify as distinct from the carrier (e.g., other active components). The compositions of the present invention preferably comprise from about 75% to about 99.999%, more preferably from about 85% to about 99.99%, still more preferably from 90% to about 99%, and most preferably, from about 93% to about 98%, by weight of the composition, of a carrier.

The cosmetic compositions of the present invention can be formulated into a wide variety of product types, including creams, waxes, pastes, lotions, milks, mousses, gels, oils, tonics, and sprays. Preferably the compounds of formula (I) are formulated into lotions, creams, gels, and sprays. These product forms may be used for a number of applications, including, but not limited to, hand and body lotions, facial moisturizers, anti-aging preparations, make-ups including foundations, and the like. Any additional components required to formulate such products vary with product type and can be routinely chosen by one skilled in the art.

If compositions of the present invention are formulated as an aerosol and applied to the skin as a spray-on product, a propellant is added to the composition.

The amount of the compound of formula (I) in the cosmetic composition can easily be adjusted by a person skilled in the art in order to achieve the desired beneficial effect. Preferably, the amount of the compound of formula (I) in the cosmetic compositions according to the present invention is at least 1 ppm based on the total weight of the cosmetic composition. In all embodiments of the present invention the amount of the compound of formula (I) is preferably selected in the range of about 0.00001 to 0.5 wt.-%, more preferably in the range of 0.0001 to 0.25 wt.-%, most preferably in the range of 0.0001 to 0.1 wt.-% based on the total weight of the cosmetic composition.

The cosmetic compositions according to the present invention can be prepared by conventional methods in the art such as e.g. by admixing a compound of formula (I) with all the definitions and preferences given herein with the cosmetically acceptable carrier. The cosmetic compositions of the invention (including the carrier) may comprise further conventional cosmetic adjuvants and additives, such as preservatives/antioxidants, fatty substances/oils, water, organic solvents, silicones, thickeners, softeners, emulsifiers, antifoaming agents, aesthetic components such as fragrances, fillers, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

To be incorporated into a cosmetic composition, the compounds of formula (I) may be used as such or in the form of a pre-mixed blend, which is often advantageous as it facilitates industrial handling.

Preferably, the compounds of formula (I) are used in the form of a pre-mixed blend, which blend consists essentially of a compound of formula (I), a cosmetically acceptable solvent wherein the solvent is preferably selected from the group consisting of water, glycerin, propanediol, caprylic/capric triglyceride, dicaprylyl carbonate, squalane and dicaprylyl ether as well as mixtures thereof and optionally a preservative wherein the preservative is preferably selected from the group consisting of phenoxyethanol, ethylhexyl glycerine, potassium sorbate and sodium benzoate as well as mixtures thereof.

The concentration of the compound of formula (I) according to the present invention in such a pre-mixed blend is preferably selected in the range of 0.001 to 10 wt.-%, more preferably in the range of 0.01 to 5 wt.-%, most preferably in the range of 0.05 to 1 wt.-%.

In a particular advantageous embodiment, a compound of formula (I) according to the present invention is provided in the form of a pre-mixed blend in propane-1,3-diol (e.g. commercially available at DuPont Tate & Lyle under the tradename ZEMEA®) as no preservative is needed to assure shelf-life of such a pre-mixed blend, which is highly appreciated in the cosmetic industry.

In accordance with the present invention, the cosmetic compositions according to the invention may also comprise further cosmetically active ingredients conventionally used in cosmetic compositions. Exemplary active ingredients encompass skin lightening agents; UV-filters, agents for the treatment of hyperpigmentation; agents for the prevention or reduction of inflammation; firming, moisturizing, soothing, and/or energizing agents as well as agents to improve elasticity and skin barrier.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the cosmetic excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

The cosmetic compositions according to the present invention may be in the form of a suspension or dispersion in solvents or fatty substances, or alternatively in the form of an emulsion or micro emulsion (in particular of oil-in-water (O/W) or water-in-oil (W/O) type, silicone-in-water (Si/W) or water-in-silicone (W/Si) type, PIT-emulsion, multiple emulsion (e.g. oil-in-water-in oil (O/W/O) or water-in-oil-in-water (W/O/W) type), pickering emulsion, hydrogel, alcoholic gel, lipogel, one- or multiphase solution or vesicular dispersion or other usual forms, which can also be applied by pens, as masks or as sprays.

If the cosmetic composition is an emulsion, such as in particular an O/W, W/O, Si/W, W/Si, O/W/O, W/O/W multiple or a pickering emulsion, then the amount of the oily phase present in such cosmetic emulsions is preferably at least 10 wt.-%, such as in the range of 10 to 60 wt.-%, preferably in the range of 15 to 50 wt.-%, most preferably in the range of 15 to 40 wt.-%, based on the total weight of the cosmetic composition.

In one embodiment, the cosmetic compositions according to the present invention are advantageously in the form of an oil-in-water (O/W) emulsion comprising an oily phase dispersed in an aqueous phase in the presence of an O/W emulsifier. The preparation of such O/W emulsions is well known to a person skilled in the art.

If the cosmetic composition according to the invention is an O/W emulsion, then it contains advantageously at least one O/W- or Si/W-emulsifier selected from the list of, glyceryl stearate citrate, glyceryl stearate SE (self-emulsifying), stearic acid, salts of stearic acid, polyglyceryl-3-methylglycosedistearate. Further suitable emulsifiers are phosphate esters and the salts thereof such as cetyl phosphate (e.g. as Amphisol® A from DSM Nutritional Products Ltd.), diethanolamine cetyl phosphate (e.g. as Amphisol® DEA from DSM Nutritional Products Ltd.), potassium cetyl phosphate (e.g. as Amphisol® K from DSM Nutritional Products Ltd.), sodium cetearylsulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, cetearyl glucoside, lauryl glucoside, decyl glucoside, sodium stearoyl glutamate, sucrose polystearate and hydrated polyisobutene. Furthermore, one or more synthetic polymers may be used as an emulsifier. For example, PVP eicosene copolymer, acrylates/C10-30 alkyl acrylate crosspolymer, and mixtures thereof.

The at least one O/W, respectively Si/W emulsifier is preferably used in an amount of 0.5 to 10 wt. %, in particular in the range of 0.5 to 6 wt.-%, such as more in particular in the range of 0.5 to 5 wt.-%, such as most in particular in the range of 1 to 4 wt.-%, based on the total weight of the cosmetic composition.

Particular suitable O/W emulsifiers to be used in the cosmetic compositions according to the invention encompass phosphate ester emulsifiers such as advantageously 8-10 alkyl ethyl phosphate, C9-15 alkyl phosphate, ceteareth-2 phosphate, ceteareth-5 phosphate, ceteth-8 phosphate, ceteth-10 phosphate, cetyl phosphate, C6-10 pareth-4 phosphate, C12-15 pareth-2 phosphate, C12-15 pareth-3 phosphate, DEA-ceteareth-2 phosphate, DEA-cetyl phosphate, DEA-oleth-3 phosphate, potassium cetyl phosphate, deceth-4 phosphate, deceth-6 phosphate and trilaureth-4 phosphate.

A particular suitable O/W emulsifier to be used in the cosmetic compositions according to the invention is potassium cetyl phosphate e.g. commercially available as Amphisol® K at DSM Nutritional Products Ltd Kaiseraugst.

Another particular suitable class of O/W emulsifiers are non-ionic self-emulsifying systems derived from olive oil e.g. known as (INCI Name) cetearyl olivate and sorbitan olivate (chemical composition: sorbitan ester and cetearyl ester of olive oil fatty acids) sold under the tradename OLIVEM 1000.

In one particular embodiment, the invention relates to cosmetic compositions with all the definitions and preferences given herein in the form of O/W emulsions comprising an oily phase dispersed in an aqueous phase in the presence of an O/W emulsifier wherein the O/W emulsifier is potassium cetyl phosphate. The amount of oily phase in such O/W emulsions is preferably at least 10 wt.-%, more preferably in the range of 10 to 60 wt.-%, most preferably in the range of 15 to 50 wt.-%, such as in the range of 15 to 40 wt.-%.

The cosmetic compositions according to the invention in general have a pH in the range of 3 to 10, preferably a pH in the range of 4 to 8 and most preferably a pH in the range of 4 to 7.5. The pH can easily be adjusted as desired with suitable acids, such as e.g. citric acid, or bases, such as sodium hydroxide (e.g. as aqueous solution), triethanolamine (TEA Care), Tromethamine (Trizma Base) and Aminomethyl Propanol (AMP-Ultra PC 2000), according to standard methods in the art.

The amount of the cosmetic composition to be applied to the skin is not critical and can easily be adjusted by a person skilled in the art. Preferably the amount is selected in the range of 0.1 to 3 mg/cm$^2$ skin, such as preferably in the range of 0.1 to 2 mg/cm$^2$ skin and most preferably in the range of 0.5 to 2 mg/cm$^2$ skin.

Further suitable uses of the compounds according to the present invention encompass pharmaceutical applications. Thus, the compounds according to the present invention may be used to prepare a pharmaceutical composition for the treatment, prevention and/or prophylaxis of any disorder and disease where it is desirable to inhibit 11β-HSD1 in a patient in need thereof such as e.g. for the treatment, prevention and/or prophylaxis of conditions, disorders or diseases of the metabolic syndrome, insulin resistance, dyslipidemia, hypertension, obesity, type 2 diabetes, impaired glucose tolerance (IGT), impaired fasting glucose as well as diabetic complications including cardiovascular diseases, arteriosclerosis, atherosclerosis, neurodegenerative and psychiatric disorders. The compounds according to the present invention may also be useful to delay or prevent the progression from IGT to type 2 diabetes as well as metabolic syndrome into type 2 diabetes.

The invention is further illustrated with reference to the following, non-limiting examples, in which all percentages are by weight based on total weight unless otherwise specified.

EXPERIMENTAL PART

1. General Information

Abbreviations:

| | |
|---|---|
| AcOEt | ethyl acetate |
| Boc$_2$O | di-tert-butyl-dicarbonate |
| DCM | dichloromethane |
| DIEA | N,N-diisopropylethylamine |
| DMAP | N,N-dimethylaminopyridine |
| DME | 1,2-dimethoxyethane |
| EDC•HCl | N-(3-dimethylaminopropyl)-N'-ethylcarbodiimide hydrochloride |
| EtOH | ethanol |
| HOBt | 1-hydroxybenzotriazole |
| MeCN | acetonitrile |
| Py | pyridine |

-continued

| TBAB | tetra-n-butylammonium bromide |
| tBu | tert-butyl |
| TFA | trifluoroacetic acid |
| EDTA | ethylenediaminetetraacetic acid |
| EGTA | ethylene glycol bis(2-aminoethylether) tetraacetic acid |
| HEPES | 4-(2-hydroxyethyl)-1-piperazineethanesulfonic acid |
| NADPH | nicotinamide adenine dinucleotide phosphate |
| Tris | tris(hydroxymethyl)aminomethane |
| DMSO | dimethyl sulfoxide |
| TLC | Thin Layer Chromatography |
| tr | retention time |

Low-resolution mass-spectra (LR-MS): measured on a Waters Acquity I-Class Ultra Performance Liquid Chromatography, equipped with an Acquity HSS T3 100 Å, 1.8 µm 2.1×50 mm² analytical column and a photodiode array (PDA) detector operating in the 200-400 nm wavelength range coupled to a Waters Single Quadrupole Detector mass spectrometer operating in positive electrospray ionization (ESI+) mode and detecting in the m/z range 100-1500. $H_2O+0.04\%$ HCOOH (A' phase) and MeCN+0.04% HCOOH (B' phase) were used as eluents, with a flow of 0.6 mL/min.

Analytical chromatograms for solubility tests: measured on a Waters Acquity Ultra Performance Liquid Chromatography (UPLC), equipped with an Acquity HSS T3 100 Å, 1.8 µm 2.1×50 mm² analytical column and a PDA detector operating in the 200-400 nm wavelength range. $H_2O+0.02\%$ TFA (A phase) and MeCN+0.02% TFA (B phase) were used as eluents, with a flow of 0.5 mL/min.

Preparative HPLC purifications: performed on a Waters High Performance Liquid Chromatography LC-2525 equipped with a Waters 2767 Sample Manager and a Waters FCII automated fraction collector, using a Grom Saphir 110 C18 10 µm 50×300 mm² preparative column and a Waters 2487 double wavelength UV-Vis detector operating at 220 and 254 nm.

$H_2O+0.07\%$ TFA (A" phase) and MeCN+0.07% TFA (B" phase) were used as eluents, with a flow of 55 mL/min.

General Synthesis Strategies

Where not otherwise stated, the reported analogues were synthesized by means of one of the following four general two-step synthesis strategies; literature protocols[1-3] as outlined below were applied for the Suzuki Ar—Ar cross-coupling reactions as indicated. All air- and water-sensitive reactions, including Suzuki cross-couplings, were performed under argon. Dichloromethane for amidation reactions was dried over sodium sulfate and stored under argon. Diethyl ether was dried over phosphoric anhydride and stored under argon.

MilliQ water for cross-coupling reaction was degassed by sparging with argon under vacuum for 30 minutes prior to use. The catalytic 10 mM Pd(EDTA) solution was prepared from palladium(II) chloride, ethylenediaminetetraacetic acid disodium dihydrate and sodium carbonate as described in D. N. Korolev, N. A. Bumagin, *Tetrahedron Lett.* 46, 5751 (2006).

LITERATURE PROTOCOLS (1) D. N. Korolev, N. A. Bumagin, *Tetrahedron Lett.* 46, 5751 (2006)
(2) M. Venkatraj, J. Messagie, J. Joossens, A.-M. Lambeir, A. Haemers, P. Van der Veken, K. Augustyns, *Bioorg. Med. Chem.* 20, 1557 (2012)

(3) M. J. Burk, J. R. Lee, J. P. Martinez, *J. Am. Chem. Soc.* 114, 10847 (1994)

Strategy A

Step A1: In a round-bottomed flask 3-bromobenzoic acid is dissolved in anhydrous DCM (5 mL/mmol) under stirring at room temperature, HOBt (1.11 eq) and EDC.HCl (1.10 eq) are added. After the activation is quantitative (as judged by ultra high-performance liquid chromatography analysis), the required secondary amine (1.2 eq) and DIEA (1.5 eq) are added. After 30 min the mixture is concentrated under reduced pressure, taken-up with AcOEt (40 mL/mmol 3-bromobenzoic acid), washed with 5% $KHSO_4$ (2×15 mL/mmol 3-bromobenzoic acid), $H_2O$ (12 mL/mmol 3-bromobenzoic acid), 5% $NaHCO_3$ (3×12 mL/mmol 3-bromobenzoic acid) and brine (12 mL/mmol 3-bromobenzoic acid), dried over $Na_2SO_4$, filtered and evaporated to dryness under reduced pressure.

Step A2[2]: The aryl bromide derivative obtained in step A1, the required aryl boronic acid (1.1 eq), $K_2CO_3$ (3 eq) and palladium(0) tetrakis(triphenylphosphine) (0.02 eq) are given in this order in a screw-cap reactor, a 8:8:1 toluene/EtOH/$H_2O$ mixture (8.5 mL/mmol aryl bromide) is added, the reactor is closed tightly and heated to 100° C. under stirring. After 4 h the mixture is cooled to room temperature, diluted with $H_2O$ (12 mL/mmol aryl bromide), and extracted with AcOEt (2×25 mL/mmol aryl bromide), the pooled organic phases are washed with 5% $NaHCO_3$ (2×12 mL/mmol aryl bromide) and brine (12 mL/mmol aryl bromide), dried over $Na_2SO_4$, filtered and evaporated to dryness under reduced pressure. If necessary, the crude product is purified by preparative HPLC.

Strategy B

Step B1: To a suspension of 3-carboxyphenylboronic acid in a 3:2 mixture of DCM/MeCN (anhydrous, 5 mL/mmol) HOBt (1.11 eq) and EDC.HCl (1.10 eq) are added. After complete dissolution the required secondary amine (1.2 eq) and DIEA (1.5 eq) are added. After 30 min the mixture is concentrated under reduced pressure, taken-up with AcOEt (40 mL/mmol boronic acid), washed with 2.5% $KHSO_4$ (6×10 mL/mmol boronic acid), $H_2O$ (2×12 mL/mmol boronic acid) and brine (12 mL/mmol boronic acid), dried over $Na_2SO_4$, filtered and evaporated to dryness under reduced pressure.

If necessary, the crude product is purified by preparative HPLC.

Step B2[1]: The required aryl bromide, the aryl boronic acid derivative obtained in step B1 (1.05 eq), $Na_2CO_3$ (2 eq) and TBAB (0.01 eq) are given in this order in a screw-cap reactor. $H_2O$ (2.0 mL/mmol aryl bromide) and 10 mM Pd(EDTA) solution (0.3 mL/mmol aryl bromide) are added, the reactor is closed tightly and heated to 100° C. under stirring. After 5 h the mixture is cooled to room temperature, diluted with AcOEt (40 mL/mmol aryl bromide), washed with 5% $NaHCO_3$ (15 mL/mmol aryl bromide), $H_2O$ (15 mL/mmol aryl bromide), 5% $KHSO_4$ (15 mL/mmol aryl bromide) and brine (15 mL/mmol aryl bromide), dried over $Na_2SO_4$, filtered and evaporated to dryness under reduced pressure.

If necessary, the crude product is purified by preparative HPLC.

Strategy C

Step C1[2]: 3-bromobenzoic acid, the required aryl boronic acid (1.1 eq), $K_2CO_3$ (3 eq) and palladium(0) tetrakis(triphenylphosphine) are given in a screw-cap reactor, a 8:8:1 toluene/EtOH/$H_2O$ mixture (8.5 mL/mmol 3-bromobenzoic acid) is added, the reactor is closed tightly and heated to 100° C. under stirring. After 4 h the mixture is cooled to room temperature, diluted with AcOEt (10 mL/mmol 3-bromobenzoic acid) and extracted with 5% NaHCO$_3$ (4×10 mL/mmol 3-bromobenzoic acid). The pooled basic extracts are acidified to pH 3 by dropwise addition of concentrated HCl under stirring, then extracted with AcOEt (3×10 mL/mmol 3-bromobenzoic acid). The pooled organic extracts are washed with water (10 mL/mmol 3-bromobenzoic acid) and brine (10 mL/mmol 3-bromobenzoic acid), dried over Na$_2$SO$_4$, filtered and evaporated to dryness under reduced pressure.

Step C2: To a suspension of the benzoic acid derivative obtained in step C1 in anhydrous DCM (5 mL/mmol) in a round-bottomed flask HOBt (1.11 eq) and EDC.HCl (1.10 eq) are added. After complete dissolution the required secondary amine (1.2 eq) and DIEA (1.5 eq) are added. After 30 min the mixture is concentrated under reduced pressure, taken-up with AcOEt (40 mL/mmol benzoic acid), washed with 5% KHSO$_4$ (2×15 mL/mmol benzoic acid), H$_2$O (12 mL/mmol benzoic acid), 5% NaHCO$_3$ (3×12 mL/mmol benzoic acid) and brine (12 mL/mmol benzoic acid), dried over Na$_2$SO$_4$, filtered and evaporated to dryness under reduced pressure.

Strategy D

Step D1[1]: The required aryl bromide, 3-carboxyphenylboronic acid (1.05 eq), Na$_2$CO$_3$ (2 eq), TBAB (0.01 eq) are given in a screw-cap reactor. H$_2$O (2 mL/mmol aryl bromide) and 10 mM Pd(EDTA) solution (0.3 mL/mmol aryl bromide) are added, the reactor is closed tightly and heated to 100° C. under stirring. After 5 hours the mixture is cooled to room temperature, diluted with AcOEt (10 mL/mmol aryl bromide) and extracted with 5% NaHCO$_3$ (4×10 mL/mmol aryl bromide). The pooled basic extracts are acidified to pH 3 by dropwise addition of concentrated HCl under stirring, then extracted with AcOEt (3×10 mL/mmol aryl bromide). The pooled organic extracts are washed with H$_2$O (10 mL/mmol aryl bromide) and brine (10 mL/mmol aryl bromide), dried over Na$_2$SO$_4$, filtered and evaporated to dryness under reduced pressure.

If necessary, the crude product is purified by preparative-HPLC.

Step D2: To a suspension of the benzoic acid derivative obtained in step D1 in anhydrous DCM (5 mL/mmol) in a round-bottomed flask HOBt (1.11 eq) and EDC.HCl (1.10 eq) are added. After complete dissolution the required secondary amine (1.2 eq) and DIEA (1.5 eq) are added. After 30 min the mixture is concentrated under reduced pressure, taken-up with AcOEt (40 mL/mmol benzoic acid), washed with 5% KHSO$_4$ (2×15 mL/mmol benzoic acid), H$_2$O (12 mL/mmol benzoic acid), 5% NaHCO$_3$ (3×12 mL/mmol benzoic acid) and brine (12 mL/mmol benzoic acid), dried over Na$_2$SO$_4$, filtered and evaporated to dryness under reduced pressure.

2. Synthesized Compounds

Example 1 (4-Methylpiperidin-1-yl)(3-(6-methylpyridin-3-yl)phenyl)methanone (II-a)

The derivative was prepared following general strategy D; work-up in step D1 and reaction conditions for amide formation in step D2 were modified due to the basicity of the intermediate.

Step D1: The reaction was performed with the standard protocol using 178 mg 3-carboxyphenylboronic acid (1.05 mmol) and 176 mg 5-bromo-2-methylpyridine (1.0 mmol). After acidification of the basic extracts, the aqueous phase was saturated with NaCl and extracted with 1-butanol (4×10 mL). The pooled organic extracts were washed with brine (10 mL), dried over Na$_2$SO$_4$, filtered, concentrated under reduced pressure, taken-up with toluene (5 mL) and evaporated to dryness under reduced pressure. 222 mg 3-(6'-methylpyridin-3'-yl)-benzoic acid hydrochloride were obtained (85% yield). LR-MS: m/z 214.1 ([M+H]$^+$, clc 214.09).

Step D2: To a suspension of 210 mg 3-(6'-methylpyridin-3'-yl)-benzoic acid hydrochloride (0.81 mmol) in a 2:1 DCM/MeCN mixture (6 mL) in a round-bottomed flask 0.15 mL DIEA (0.89 mmol) were added. After 5 min 186 mg HOBt (1.37 mmol) and 264 mg EDC.HCl (1.35 mmol) were added under stirring. After 30 min 147 µL 4-methylpiperidine (0.98 mmol) and 0.21 mL DIEA (1.24 mmol) were added. After 50 min the mixture was concentrated under reduced pressure, taken-up with AcOEt (45 mL), washed with 5% NaHCO$_3$ (4×15 mL) and H$_2$O (15 mL) and extracted with 5% KHSO$_4$ (2×22 mL). The pooled acidic extracts were brought to pH 8 by addition of solid Na$_2$CO$_3$ and extracted with AcOEt (4×15 mL), the pooled organic extracts were washed with H$_2$O (10 mL) and brine (10 mL), dried over Na$_2$SO$_4$, filtered and evaporated to dryness under reduced pressure. 181 mg product II-a were obtained (74% yield).

LR-MS: m/z 295.2 ([M+H]$^+$, clc 295.18).

Example 2 (4-Methylpiperidin-1-yl)(4'-hydroxy-[1,1'-biphenyl]3-yl)methanone (II-b)

The derivative was prepared following general strategy D; one preliminary protection step and one final deprotection step were required and a different literature protocol[2] for the cross-coupling in step D1 was applied.

Protection step: To a solution of 874 mg 4-bromophenol (5.0 mmol) in 10 mL anhydrous DCM and 0.49 mL py (6.0 mmol) in a round-bottomed flask 12.3 mg DMAP (0.1 mmol) and 1.20 g Boc$_2$O (5.3 mmol) were added. After 30 min CO$_2$ evolution ceased, the mixture was concentrated under reduced pressure, taken-up in AcOEt (50 mL), washed with 5% KHSO$_4$ (2×25 mL), H$_2$O (18 mL), 5% Na$_2$CO$_3$ (2×25 mL) and brine (18 mL), then dried over Na$_2$SO$_4$, filtered and evaporated to dryness under reduced pressure. 1.25 g 4-bromophenyl-tert-butylcarbonate were obtained (91% yield).

Step 1: 276 mg 4-bromophenyl-tert-butylcarbonate (1.0 mmol), 186 mg 3-carboxyphenylboronic acid (1.05 mmol), 419 mg K$_2$CO$_3$ (3.0 mmol) and 23 mg palladium(0) tetrakis(triphenylphosphine) (0.02 mmol) were given in a screw-cap reactor, 8.5 mL of a 8:8:1 toluene/EtOH/H$_2$O mixture were added, the reactor was closed tightly and heated to 100° C. under stirring. After 4 h the mixture was cooled to room temperature, diluted with AcOEt (10 mL) and extracted with 3% Na$_2$CO$_3$ (4×15 mL). The pooled basic extracts were acidified to pH 3 by dropwise addition of 6 N HCl under stirring, whereas a solid precipitated, which was filtered and washed with 6 N HCl and H$_2$O. The crude product was dissolved in AcOEt (30 mL), washed H$_2$O (10 mL) and brine (10 mL), then dried over Na$_2$SO$_4$, filtered and evaporated to dryness under reduced pressure. 150 mg 3-(4'-tert-butyloxycarbonyloxyphenyl)-benzoic acid were obtained (46% yield).

Step D2: The reaction was performed using 142 mg 3-(4'-tert-butyloxycarbonyloxyphenyl)-benzoic acid (0.44 mmol) and 65 µL 4-methylpiperidine (0.53 mmol). 180 mg N-(3'-(4''-tert-butyloxycarbonyloxyphenyl)-benzoyl)-4-methylpiperidine were obtained (quantitative yield). LR-MS: m/z 396.2 ([M+H]$^+$, clc 396.22).

Deprotection step: 172 mg N-(3'-(4''-tert-butyloxycarbonyloxyphenyl)-benzoyl)-4-methylpiperidine were dissolved under argon in 2 mL of a 4:1 DCM/95% TFA$_{(aq)}$ mixture in a round-bottomed flask. After stirring for 2 h at room temperature the mixture was stripped with nitrogen; the residue was taken-up in DCM and stripped with nitrogen 3 more times. The residue was taken-up with Et$_2$O and evaporated under reduced pressure; this was repeated 2 times, until a solid was obtained. 125 mg product II-b were obtained (98% yield).

LR-MS: m/z 296.2 ([M+H]$^+$, clc 296.17).

Example 3 (4'-Fluoro-[1,1'-biphenyl]-3-yl)(4-methylpiperidin-1-yl)methanone (II-c)

The derivative was prepared following general strategy D.

Step D1: The reaction was performed using 178 mg 3-carboxyphenylboronic acid (1.05 mmol) and 111 μL 1-bromo-4-fluorobenzene (1.0 mmol). 190 mg 3-(4'-fluorophenyl)-benzoic acid were obtained (86% yield).

Step D2: The reaction was performed using 180 mg 3-(4'-fluorophenyl)-benzoic acid (0.83 mmol) and 123 μL 4-methylpiperidine (1.00 mmol). 215 mg product II-c were obtained (85% yield).

LR-MS: m/z 298.2 ([M+H]$^+$, clc 298.18).

Example 4 (3'-fluoro-4'-methyl-[1,1'-biphenyl]-3-yl)(4-methylpiperidin-1-yl)methanone (II-d)

The derivative was prepared following general strategy B; a different literature protocol[2] was applied for the cross-coupling in step B2.

Step B1: The reaction was performed using 169 mg 3-carboxyphenylboronic acid (1.0 mmol) and 148 μL 4-methylpiperidine (1.2 mmol). 108 mg N-(3-boronobenzoyl)-4-methylpiperidine were obtained (42% yield).

Step B2: 101 mg N-(3-boronobenzoyl)-4-methylpiperidine (0.41 mmol), 50 μL 4-bromo-3-fluorotoluene (0.39 mmol), 162 mg K$_2$CO$_3$ (1.16 mmol) and palladium(0) tetrakis(triphenylphosphine) (7.7 μmol) were given in a screw-cap reactor, 3.4 mL of a 8:8:1 mixture of toluene/EtOH/H$_2$O were added, the reactor was closed tightly and heated to 100° C. under stirring. After 3 h the mixture was cooled to room temperature, diluted with H$_2$O (5 mL) and extracted with AcOEt (2×10 mL), the pooled organic phases were washed with 5% NaHCO$_3$ (10 mL) and brine (5 mL), dried over Na$_2$SO$_4$, filtered and evaporated to dryness under reduced pressure. The crude product was purified by preparative HPLC. 89 mg of compound II-d were obtained (74% yield). LR-MS: m/z 312.3 ([M+H]$^+$, clc 312.18).

Example 5 (2'-Chloro-[1,1'-biphenyl]-3-yl)(4-methylpiperidin-1-yl)methanone (II-e)

The derivative was prepared following general strategy D.

Step D1: The reaction was performed using 356 mg 3-carboxyphenylboronic acid (2.1 mmol) and 236 μL 1-bromo-2-chlorobenzene (2.0 mmol). 203 mg 3-(2'-chlorophenyl)-benzoic acid were obtained after preparative HPLC purification (44% yield).

Step D2: The reaction was performed using 62 mg 3-(2'-chlorophenyl)-benzoic acid (0.26 mmol) and 40 μL 4-methylpiperidine (0.32 mmol). 68 mg product II-e were obtained (82% yield).

LR-MS: m/z 314.2 ([M($^{35}$Cl)+H]$^+$, clc 314.13), 316.2 ([M($^{37}$Cl)+H]$^+$, clc 316.13).

Example 6 (4'-Methyl-[1,1'-biphenyl]-3-yl)(4-methylpiperidin-1-yl)methanone (II-f)

The derivative was prepared following general strategy D; a different literature protocol[2] was applied for the cross-coupling in step D1

Step D1: 186 mg 3-carboxyphenylboronic acid (1.05 mmol), 126 μL 4-bromotoluene (1.0 mmol), 417 mg K$_2$CO$_3$ (3.0 mmol) and 23 mg palladium(0) tetrakis(triphenylphosphine) (0.02 mmol) were given in a screw-cap reactor, 8.5 mL of a 8:8:1 toluene/EtOH/H$_2$O mixture were added, the reactor was closed tightly and heated to 100° C. under stirring. After 4 h the mixture was cooled to room temperature, diluted with AcOEt (10 mL) and extracted with 2% NaHCO$_3$ (4×10 mL). The pooled basic extracts were acidified to pH 3 by dropwise addition of 6 N HCl under stirring and extracted with AcOEt (3×12 mL), the pooled organic extracts were washed H$_2$O (10 mL) and brine (10 mL), then dried over Na$_2$SO$_4$, filtered and evaporated to dryness under reduced pressure. The crude product was purified by preparative HPLC, yielding 128 mg 3-(4'-tolyl)-benzoic acid (60% yield).

Step D2: The reaction was performed using 128 mg 3-(4'-tolyl)-benzoic acid (0.60 mmol) and 89 μL 4-methylpiperidine (0.72 mmol). 154 mg product II-f were obtained (87% yield).

LR-MS: m/z 294.3 ([M+H]+, clc 294.19).

Example 7 (4'-Chloro-[1,1'-biphenyl]-3-yl)(4-methylpiperidin-1-yl)methanone (II-g)

The derivative was prepared following general strategy D.

Step D1: The reaction was performed using 178 mg 3-carboxyphenylboronic acid (1.05 mmol) and 193 mg 1-bromo-4-chlorobenzene (1.0 mmol). 94 mg 3-(4'-chlorophenyl)-benzoic acid were obtained after preparative HPLC purification (39% yield).

Step D2: The reaction was performed using 87 mg 3-(4'-chlorophenyl)-benzoic acid (0.36 mmol) and 53 μL 4-methylpiperidine (0.43 mmol). 112 mg product II-g were obtained (quantitative yield).

LR-MS: m/z 314.2 ([M($^{35}$Cl)+H]$^+$, clc 314.13), 316.2 ([M($^{37}$Cl)+H]$^+$, clc 316.13).

Example 8 (3,3-Dimethylpiperidin-1-yl)(3'-fluoro-4'-methyl-[1,1'-biphenyl]-3-yl)methanone (II-h)

The derivative was prepared following general strategy D; a different protocol was applied for amide formation in step D2.

Step D1: The reaction was performed using 178 mg 3-carboxyphenylboronic acid (1.05 mmol) and 129 μL 4-bromo-2-fluorotoluene (1.0 mmol). 205 mg 3-(3'-fluoro-4'-methylphenyl)-benzoic acid were obtained (87% yield).

Step D2: To a suspension of 165 mg 3-(2'-fluoro-4'-methylphenyl)-benzoic acid (0.68 mmol) in 6 mL of a 5:1 DCM/MeCN mixture in a round-bottomed flask 101 mg HOBt (0.74 mmol) and 144 mg EDC.HCl (0.73 mmol) were added under stirring. After 15 min 98 μL 3,3-dimethylpiperidine (0.67 mmol) and 0.14 mL DIEA (0.78 mmol) were added. After 1.2 h the mixture was concentrated under reduced pressure, taken-up in AcOEt (40 mL), washed with 5% KHSO$_4$ (2×18 mL), H$_2$O (12 mL), 5% NaHCO$_3$ (3×13 mL) and brine (12 mL), dried over Na$_2$SO$_4$, filtered and evaporated to dryness under reduced pressure. 208 mg product 11-h were obtained (94% yield). LR-MS: m/z 326.2 ([M+H]$^+$, clc 326.19).

Example 9 3'-(4-methylpiperidine-1-carbonyl)-[1,1'-biphenyl]4-carboxamide (II-i)

The derivative was prepared following general strategy D; the aryl bromide building block for step D1 was prepared in-house and a modified work-up was applied in step D1. Preparation of the aryl bromide building block: In a round-bottomed two-neck flask 812 mg 4-bromobenzoic acid (4.0 mmol) were suspended in 14 mL of a 6:1 DCM/MeCN mixture under argon and 600 mg HOBt (4.44 mmol) and 861 mg EDC.HCl (4.4 mmol) were added under stirring. After 10 min the mixture became clear and was cooled to 0° C. in an ice bath. In a round-bottomed flask 1.64 g NaOH (40 mmol) were added to 2.8 mL of a 28% $NH_4OH$ solution (20 mmol) and the resulting gaseous $NH_3$ was bubbled into the reaction vessel after passing through a NaOH trap. After $NH_3$-bubbling had ceased the mixture was concentrated under reduced pressure, taken-up in AcOEt (60 mL), washed with 5% $KHSO_4$ (2×30 mL), $H_2O$ (20 mL), 5% $NaHCO_3$ (3×20 mL) and brine (20 mL), dried over $Na_2SO_4$, filtered and evaporated to dryness under reduced pressure. 636 mg 4-bromobenzamide were obtained (79% yield).

Step D1: The reaction was performed using 178 mg 3-carboxyphenylboronic acid (1.05 mmol) and 202 mg 4-bromobenzamide (1.00 mmol). After 4 h at 100° C. the reaction mixture was cooled to room temperature, diluted with AcOEt (10 mL), extracted with 5% $NaHCO_3$ (3×15 mL) and the pooled basic extracts were acidified to pH 3 by dropwise addition of concentrated HCl under stirring, whereas precipitation occurred. The precipitate was filtered and washed with 0.05 N HCl (20 mL) and with $Et_2O$ (10 mL). 227 mg 3-(4'-aminocarbonylphenyl)-benzoic acid were obtained (93% yield).

Step D2: The reaction was performed using 220 mg 3-(4-aminocarbonylphenyl)-benzoic acid (0.89 mmol) and 132 μL 4-methylpiperidine (1.07 mmol). 188 mg product II-i were obtained (64% yield). LR-MS: m/z 323.2 ([M+H]$^+$, clc 323.18).

Example 10 (4-Methylpiperidin-1-yl)(3'-hydroxy-[1,1'-biphenyl]-3-yl)methanone (II-j)

The derivative was prepared following general strategy D.
Step D1: The reaction was performed using 178 mg 3-carboxyphenylboronic acid (1.05 mmol) and 112 μL 3-bromophenol (1.0 mmol). 183 mg 3-(3'-hydroxyphenyl)-benzoic acid were obtained (84% yield).

Step D2: The reaction was performed using 188 mg 3-(3'-hydroxyphenyl)-benzoic acid (0.94 mmol) and 130 μL 4-methylpiperidine (1.05 mmol). 295 mg product II-j (oil) were obtained (quantitative yield, according to NMR analysis the product contained about 11% solvent).
LR-MS: m/z 296.2 ([M+H]$^+$, clc 296.17).

Example 11 3'-(4-Methylpiperidine-1-carbonyl)-[1,1'-biphenyl]-3-carboxamide (II-k)

The derivative was prepared following general strategy D; the aryl bromide building block for step D1 was prepared in-house and a modified work-up was applied in step D1. Preparation of the aryl bromide building block: In a round-bottomed two-neck flask 820 mg 3-bromobenzoic acid (4.0 mmol) were suspended in 14 mL of a 6:1 DCM/MeCN mixture under argon and 600 mg HOBt (4.44 mmol) and 861 mg EDC.HCl (4.4 mmol) were added under stirring. After 10 min the mixture became clear and was cooled to 0° C. in an ice bath. In a round-bottomed flask 1.64 g NaOH (40 mmol) were added to 2.8 mL of a 28% $NH_4OH$ solution (20 mmol) and the resulting gaseous $NH_3$ was bubbled into the reaction vessel after passing through a NaOH trap. After $NH_3$-bubbling had ceased, the mixture was concentrated under reduced pressure, taken-up in AcOEt (60 mL), washed with 5% $KHSO_4$ (2×30 mL), $H_2O$ (20 mL), 5% $NaHCO_3$ (3×20 mL) and brine (20 mL), dried over $Na_2SO_4$, filtered and evaporated to dryness under reduced pressure. 700 mg 3-bromobenzamide were obtained (87% yield).

Step D1: The reaction was performed using 178 mg 3-carboxyphenylboronic acid (1.05 mmol) and 201 mg 3-bromobenzamide (1.00 mmol). After 4 h at 100° C. the reaction mixture was cooled to room temperature, diluted with AcOEt (10 mL), extracted with 5% $NaHCO_3$ (3×15 mL) and the pooled basic extracts were acidified to pH 3 by dropwise addition of concentrated HCl under stirring, whereas precipitation occurred. The precipitate was filtered and washed with 0.01 N HCl (20 mL) and with cold MeCN (5 mL). 221 mg 3-(3'-aminocarbonylphenyl)-benzoic acid were obtained (90% yield).

Step D2: The reaction was performed using 211 mg 3-(3'-aminocarbonyphenyl)-benzoic acid (0.87 mmol) and 128 μL 4-methylpiperidine (1.04 mmol). 278 mg product II-k (dry foam) were obtained (93% yield, according to NMR analysis the product contained about 5% solvent).
LR-MS: m/z 323.2 ([M+H]$^+$, clc 323.18).

Example 12 (2,2-Dimethylmorpholino)(3'-fluoro-4'-methyl-[1,1'-biphenyl]-3-yl)methanone (III-a)

The derivative was prepared according to general strategy D, a different protocol was applied for amide formation in step D2.

Step D1: The reaction was performed using 533 mg 3-carboxyphenylboronic acid (3.15 mmol) and 387 μL 4-bromo-2-fluorotoluene (3.0 mmol). 614 mg 3-(3'-fluoro-4'-methylphenyl)-benzoic acid were obtained (87% yield).

Step D2: To a suspension of 178 mg 3-(3'-fluoro-4'-methylphenyl)-benzoic acid (0.76 mmol) in 7 mL of a 6:1 DCM/MeCN mixture in a round-bottomed flask 114 mg HOBt (0.83 mmol) and 161 mg EDC.HCl (0.83 mmol) were added and after complete dissolution 91 mg 2,2-dimethylmorpholine (0.75 mmol) were given. After stirring for 1.2 h the mixture was concentrated under reduced pressure, taken-up in AcOEt (40 mL), then washed with 5% $KHSO_4$ (2×18 mL) and $H_2O$ (12 mL). The organic phase was concentrated under reduced pressure, taken-up in 4 mL of an 1:1 MeOH/$H_2O$ mixture and 42 mg LiOH*$H_2O$ (1.0 mmol) were added, then the mixture was stirred at 50° C. to hydrolyze the unreacted active ester. After 1 h the mixture was cooled to room temperature, diluted with AcOEt (30 mL), washed with 5% $Na_2CO_3$ (5×15 mL) and brine (15 mL), dried over $Na_2SO_4$, filtered and evaporated to dryness under reduced pressure. 219 mg product III-a were obtained (88% yield).
LR-MS: m/z 328.2 ([M+H]$^+$, clc 328.17).

Example 13 (2,6-Dimethylmorpholino)(3'-fluoro-4'-methyl-[1,1'-biphenyl]-3-yl)methanone (III-b)

The derivative was prepared according to general strategy D.

Step D1: The reaction was performed using 533 mg 3-carboxyphenylboronic acid (3.15 mmol) and 387 μL 4-bromo-2-fluorotoluene (3.0 mmol). 614 mg 3-(3'-fluoro-4'-methylphenyl)-benzoic acid were obtained (87% yield).

Step D2: The reaction was performed using 183 mg 3-(3'-fluoro-4'-methylphenyl)-benzoic acid (0.79 mmol) and 121 µL 2,6-dimethylmorpholine (0.95 mmol). 251 mg product III-b were obtained (95% yield). Due to the composition of the secondary amine used, the product was obtained as a mixture of two diastereomeric pairs of enantiomers in about 4:1 ratio.

LR-MS: major diastereomer (1.59 min) m/z 328.3 ([M+H]$^+$, clc 328.17); minor diastereomer (1.62 min) m/z 328.3 ([M+H]$^+$, clc 328.17).

Example 14 2,6-Morpholino(4'-methyl-[1,1'-biphenyl]-3-yl)methanone (III-c)

The derivative was prepared following general strategy C.
Step C1: The reaction was performed using 154 mg 4-tolylboronic acid (1.05 mmol) and 205 mg 3-bromobenzoic acid (1.0 mmol). 172 mg 3-(4'-tolyl)-benzoic acid were obtained (80% yield).
Step C2: The reaction was performed using 171 mg 3-(4'-tolyl)-benzoic acid (0.79 mmol) and 121 µL 2,6-dimethylmorpholine (0.95 mmol). 216 mg product III-c were obtained (84% yield). Due to the composition of the secondary amine used, the product was obtained as a mixture of two diastereomeric pairs of enantiomers in about 4:1 ratio.

LR-MS: major diastereomer (1.57 min) m/z 310.3 ([M+H]$^+$, clc 310.19); minor diastereomer (1.62 min) m/z 310.3 ([M+H]$^+$, clc 310.19).

Example 15 Azepan-1-yl-(3'-fluoro-4'-methyl-[1,1'-biphenyl]-3-yl)methanone (IV-a)

The derivative was prepared following general strategy A; a different literature protocol[3] was applied for the cross-coupling in step A2.
Step A1: The reaction was performed using 410 mg 3-bromobenzoic acid (2.0 mmol) and 275 uL azepane (2.4 mmol). 545 mg N-(3-bromobenzoyl)-azepane were obtained (96% yield).
Step A2: 264 mg N-(3-bromobenzoyl)-azepane (0.92 mmol), 217 mg 3-fluoro-4-tolylboronic (1.36 mmol), 194 mg Na$_2$CO$_3$ (1.84 mmol), 10.4 mg PdCl$_2$ (0.046 mmol), 29.5 mg tris(2-methylphenyl)-phosphine (0.092 mmol) were given in a screw-cap reactor, DME (5.5 mL) and H$_2$O (1.0 mL) were added, the reactor was closed tightly and heated to 80° C. under stirring. After 4 h the mixture was cooled to room temperature, diluted with H$_2$O (10 mL) and extracted with AcOEt (2×20 mL), the pooled organic extracts were washed with 5% NaHCO$_3$ (2×10 mL) and brine (10 mL), dried over Na$_2$SO$_4$, filtered and evaporated to dryness under reduced pressure. The crude product was purified by preparative-HPLC. 205 mg of the compound IV-a were obtained (71% yield).

LR-MS: m/z 312.3 ([M+H]$^+$, clc 312.18).

Example 16 Azepan-1-yl(4'-chloro-[1,1'-biphenyl]-3-yl)methanone (IV-b)

The derivative was prepared following general strategy A.
Step A1: The reaction was performed using 410 mg 3-bromobenzoic acid (2.0 mmol) and 275 µL azepane (2.4 mmol). 545 mg N-(3-bromobenzoyl)-azepane were obtained (96% yield).
Step A2: The reaction was performed using 259 mg N-(3-bromobenzoyl)-azepane (0.90 mmol) and 156 mg 4-chlorophenylboronic acid (0.99 mmol). 237 mg compound IV-b were obtained after preparative HPLC purification (83% yield).

LR-MS: m/z 314.2 ([M($^{35}$Cl)+H]$^+$, clc 314.13), 316.2 ([M($^{37}$Cl)+H]$^+$, clc 316.13).

Example 17 Azepan-1-yl(4'-methyl-[1,1'-biphenyl]-3-yl)methanone (IV-c)

The derivative was prepared according to general strategy D; a different protocol was applied for amide formation in step D2.
Step D1: The reaction was performed using 178 mg 3-carboxyphenylboronic acid (1.05 mmol) and 126 µL 4-bromotoluene (1.0 mmol). 186 mg 3-(4'-tolyl)-benzoic acid were obtained (87% yield).
Step D2: 185 mg 3-(4'-tolyl)-benzoic acid (0.87 mmol) were suspended in anhydrous DCM (5 mL) in a round-bottomed flask and 0.64 mL SOCl$_2$ (8.7 mmol) were added. After 25 min a clear solution was obtained, which was stripped with argon. The residue was taken-up in anhydrous Et$_2$O and stripped with argon 4 times, then evaporated to dryness under reduced pressure. The residue was taken-up in anhydrous DCM (5 mL) and 200 µL azepane (1.80 mmol) were given. After 20 min the mixture was concentrated under reduced pressure, taken-up with AcOEt (40 mL), washed with 5% KHSO$_4$ (2×15 mL), H$_2$O (10 mL), 5% NaHCO$_3$ (2×15 mL) and brine (10 mL), then dried over Na$_2$SO$_4$, filtered and evaporated to dryness under reduced pressure. 250 mg product IV-c were obtained (97% yield).

LR-MS: m/z 294.3 ([M+H]$^+$, clc 294.19).

Example 18 Azepan-1-yl(4'-hydroxy-[1,1'-biphenyl]-3-yl)methanone (IV-d)

The derivative was prepared following general strategy B; a slightly modified work-up was applied in step 82.
Step B1: The reaction was performed using 1.016 g 3-carboxyphenylboronic acid (6.0 mmol) and 0.82 mL diazepane (7.2 mmol), 1.179 g N-(3-boronobenzoyl)-azepane were obtained after preparative HPLC purication (79% yield).
Step B2: The reaction was performed using 262 mg N-(3-boronobenzoyl)-azepane (1.05 mmol) and 175 mg 4-bromophenol (1.0 mmol). After taking-up in MeOH the crude product obtained by the usual extractive work-up 80 mg pure product IV-d (26% yield) precipitated from the mixture and were collected by filtration. Additional 99 mg product IV-d (33% yield) were obtained after preparative HPLC purification of the concentrated mother liquors (total yield 59%).

LR-MS: m/z 296.2 ([M+H]$^+$, clc 296.17).

Example 19: Azepan-1-yl(3-(6-methylpyridin-3-yl)-phenyl)methanone (IV-e)

The derivative was prepared following general strategy B.
Step B1: The reaction was performed using 1.016 g 3-carboxyphenylboronic acid (6.0 mmol) and 0.82 mL diazepane (7.2 mmol). 1.179 g N-(3-boronobenzoyl)-azepane were obtained after preparative HPLC purication (79% yield).
Step B2: The reaction was performed using 262 mg N-(3-boronobenzoyl)-azepane (1.05 mmol) and 175 mg 5-bromo-2-methylpyridine (1.0 mmol). 150 mg product IV-e were obtained after preparative HPLC purification (50% yield).

LR-MS: m/z 295.2 ([M+H]$^+$, clc 295.18).

Example 20 [1,1'-Biphenyl]-3-yl(azepan-1-yl)methanone (IV-f)

The derivative was prepared following general strategy B.

Step B1: The reaction was performed using 1.016 g 3-carboxyphenylboronic acid (6.0 mmol) and 0.82 mL azepane (7.2 mmol). 1.179 g N-(3-boronobenzoyl)-azepane were obtained after preparative HPLC purication (79% yield).

Step B2: The reaction was performed using 262 mg N-(3-boronobenzoyl)-azepane (1.05 mmol) and 106 µL bromobenzene (1.0 mmol). 250 mg product IV-f were obtained (86% yield).

LR-MS: m/z 280.2 ([M+H]$^+$, clc 280.17).

Example 21 Azepan-1-yl(3',4'-dimethyl[1,1'-biphenyl]3-yl)methanone (IV-g)

The derivative was prepared following general strategy B.

Step B1: The reaction was performed using 1.016 g 3-carboxyphenylboronic acid (6.0 mmol) and 0.82 mL azepane (7.2 mmol). 1.179 g N-(3-boronobenzoyl)-azepane were obtained after preparative HPLC purication (79% yield).

Step B2: The reaction was performed using 262 mg N-(3-boronobenzoyl)-azepane (1.05 mmol) and 136 µL 4-bromo-o-xylene (1.0 mmol). 192 mg product IV-g were obtained after preparative HPLC purification (63% yield).

LR-MS: m/z 308.3 ([M+H]$^+$, clc 308.20).

Example 22 11-beta-hydroxysteroid Dehydrogenase Type 1 Inhibition Activity

A: Cell Assay

Preparation of Cell Lysates:

Stably transfected human embryonic kidney (HEK-293) cells expressing 11β-HSD1 and hexose-6-phosphate dehydrogenase (the so called HHH7 clone) were cultivated for 48 h in Dulbecco's modified Eagle medium (DMEM) containing 4.5 g/L glucose, 10% fetal bovine serum, 100 U/mL penicillin, 0.1 mg/mL streptomycin, 1×MEM nonessential amino acids, and 10 mM HEPES buffer, pH 7.4. The cells were then washed with phosphate-buffered saline, and centrifuged for 4 min at 150×g. After removal of the supernatants, cell pellets were snap frozen on dry ice and stored at −80° C. until further use.

Activity Assay in Cell Lysates:

Cell lysates were incubated for 10 min at 37° C. in TS2 buffer (100 mM NaCl, 1 mM EGTA, 1 mM EDTA, 1 mM MgCl$_2$, 250 mM sucrose, 20 mM Tris-HCl, pH 7.4) in a final volume of 22.2 µL containing either solvent (0.1% DMSO) or the inhibitor at the respective concentration as indicated in Table 4 (see below). Enzyme activities were measured using the following conditions: 192 nM unlabeled cortisone, 8 nM radiolabeled cortisone, 450 µM NADPH.

Reactions were stopped after 10 min by adding an excess of unlabeled cortisone and cortisol (1:1, 2 mM, in methanol). The steroids were separated by TLC, using methanol-chloroform (1:9) as solvent, followed by scintillation counting and calculation of substrate concentration. Data were collected from four independent measurements (standard deviation<10%).

TABLE 4

Results of the enzyme assay

| | | 11β-HSD1 Remaining activity [% of control] | |
|---|---|---|---|
| # | Compound | 1 µM | 100 nM |
| 1 | (4-methylpiperidin-1-yl)(3-(6-methylpyridin-3-yl)phenyl)methanone (II-a) | 5 | 36 |
| 2 | (4'-hydroxy-[1,1'-biphenyl]-3-yl)(4-methylpiperidin-1-yl)methanone (II-b) | 5 | 38 |
| 3 | (4'-fluoro-[1,1'-biphenyl]-3-yl)(4-methylpiperidin-1-yl)methanone (II-c) | 4 | 43 |
| 4 | (3'-fluoro-4'-methyl-[1,1'-biphenyl]-3-yl)(4-methylpiperidin-1-yl)methanone (II-d) | 1 | 45 |
| 5 | (2'-chloro-[1,1'-biphenyl]-3-yl)(4-methylpiperidin-1-yl)methanone (II-e) | 4 | 49 |
| 6 | (4'-methyl-[1,1'-biphenyl]-3-yl)(4-methylpiperidin-1-yl)methanone (II-f) | 2 | 52 |
| 7 | (4'-chloro-[1,1'-biphenyl]-3-yl)(4-methylpiperidin-1-yl)methanone (II-g) | 3 | 58 |
| 8 | (3,3-dimethylpiperidin-1-yl)(3'-fluoro-4'-methyl-[1,1'-biphenyl]-3-yl)methanone (II-h) | 3 | 60 |
| 9 | 3'-(4-methylpiperidine-1-carbonyl)-[1,1'-biphenyl]-4-carboxamide (II-i) | 19 | 65 |
| 10 | (3'-hydroxy-[1,1'-biphenyl]-3-yl)(4-methylpiperidin-1-yl)methanone (II-j) | 8 | 70 |
| 11 | 3'-(4-methylpiperidine-1-carbonyl)-[1,1'-biphenyl]-3-carboxamide (II-k) | 34 | 89 |
| 12 | (2,2-dimethylmorpholino) (3'-fluoro-4'-methyl-[1,1'-biphenyl]-3-yl)methanone (III-a) | 1 | 14 |
| 13 | (2,6-dimethylmorpholino) (3'-fluoro-4'-methyl-[1,1'-biphenyl]-3-yl)methanone (III-b) | 4 | 44 |
| 14 | (2,6-dimethylmorpholino) (4'-methyl-[1,1'-biphenyl]-3-yl)methanone (III-c) | 3 | 60 |
| 15 | azepan-1-yl(3'-fluoro-4'-methyl-[1,1'-biphenyl]-3-yl)methanone (IV-a) | 1 | 19 |
| 16 | azepan-1-yl(4'-chloro-[1,1'-biphenyl]-3-yl)methanone (IV-b) | 2 | 50 |
| 17 | azepan-1-yl(4'-methyl-[1,1'-biphenyl]-3-yl)methanone (IV-c) | nd | 17 |
| 18 | azepan-1-yl(4'-hydroxy-[1,1'-biphenyl]-3-yl)methanone (IV-d) | nd | 28 |
| 19 | azepan-1-yl(3-(6-methylpyridin-3-yl)phenyl)methanone (IV-e) | nd | 31 |
| 20 | [1,1'-biphenyl]-3-yl(azepan-1-yl)methanone (IV-f) | nd | 21 |
| 21 | azepan-1-yl(3',4'-dimethyl-[1,1'-biphenyl]-3-yl)methanone (IV-g) | nd | 69 |

B: Human Keratinocytes Assay

Cell Culture: Primary human skin keratinocytes obtained from CelINTec advanced Cell Systems were maintained in CnT-PR medium at 37° C. in a humidified 5% CO$_2$-air atmosphere. Cells were subcultured before reaching confluence.

Assessment of 11β-HSD1 activity: Human primary keratinocytes were pre-cultured in complete culture media (CnT-PR, CelINTec) to 90% of confluence. Subsequently cells were washed twice with PBS-buffer to remove remaining corticosteroids and media were exchanged to custom made hydrocortisone-free media. Cells were then treated with 1000 nM cortisone in combination with different concentrations of inhibitors as indicated in Table A. 48 hrs later cell culture supernatant was collected and cortisol levels were assessed with the Cortisol Parameter Assay Kit (R&D Systems) following the instructions of the protocol and using a Multiskan Ascent plate reader (Labsystems).

Calculation: % remaining 11β-HSD1 activity=(cortisol-level with inhibitor/cortisol-level without inhibitor)*100%

TABLE A

| Results | | |
|---|---|---|
| Compound | Concentration [nM] | remaining 11β-HSD1 activity [%] |
| Control | 0.00 | 100 |
| (II-h) | 0.04 | 74 |
|  | 0.10 | 45 |
|  | 0.32 | 24 |
|  | 1.00 | 10 |
| (III-a) | 0.32 | 70 |
|  | 1.00 | 55 |
|  | 3.16 | 37 |
|  | 10.00 | 11 |
|  | 31.62 | 3 |
|  | 100.00 | 0 |
| (II-e) | 1.00 | 85 |
|  | 3.16 | 70 |
|  | 10.00 | 50 |
|  | 31.62 | 21 |
|  | 100.00 | 4 |
| (IV-a) | 1.00 | 74 |
|  | 3.16 | 45 |
|  | 10.00 | 22 |
|  | 31.62 | 8 |
|  | 100.00 | 2 |
| (IV-c) | 1.00 | 70 |
|  | 3.16 | 42 |
|  | 10.00 | 23 |
|  | 31.62 | 9 |
|  | 100.00 | 3 |
| (IV-f) | 1.00 | 83 |
|  | 3.16 | 73 |
|  | 10.00 | 52 |
|  | 31.62 | 28 |
|  | 100.00 | 10 |

C: Ex Vivo Assays

1. Total Dermal Collagen after Cortisone and Cortisone/Inhibitor Treatment

Human skin from abdominal plastic surgery was used. The skin samples were cut in pieces of ~8×3 mm (ø×thickness) and cultured up to day 6 in an air-liquid interface in a perforated ring of stainless steel in contact with a culture medium (modified Williams' E medium), while renewing the culture medium on day 3. Six skin specimens were used for each test sample. Each test sample (4 µl) was applied topically on top of each piece after cleaning of the surface with a cotton pad, which was subsequently covered with a 6 ø mm delivery membrane, this procedure was repeated daily. After 6 days skin sections were stained with Picrosirius Red histochemical staining, that dyes collagen fibers in purple-red. The papillary dermis was selected for the analysis. The different colors of the pictures were separated by using a deconvolution matrix. After deconvolution only pink-reddish images are used. Within these images the evaluation of dermal collagen was performed by estimating both color intensity and distribution with IMAGE J (NIH) analysis software. Two slides of each skin sample were processed by image acquisition and related analysis (i.e. 12 images for each treatment).

TABLE B

| Results of the comparison treatments versus cortisone 0.1 µl at day 6 | | | | |
|---|---|---|---|---|
| | Test sample | | | Increase |
| # | compound | conc. (in DMSO) | Dermal collagen* | versus cortisone (#2) |
| 1 | none (untreated) | 0 µM | 100% | — |
| 2 | cortisone° | 0.1 µM | 77% | — |
| 3 | (IV-a) | 10 µM | 96% | +25% |
| 4 |  | 100 µM | 97% | +26% |
| 5 |  | 200 µM | 86% | +12% |
| 6 | (IV-e) | 10 µM | 103% | +34% |
| 7 |  | 100 µM | 101% | +31% |
| 8 |  | 200 µM | 96% | +25% |
| 9 | (IV-f) | 10 µM | 103% | +34% |
| 10 |  | 100 µM | 103% | +34% |
| 11 |  | 200 µM | 93% | +21% |
| 12 | (II-a) | 10 µM | 94% | +22% |
| 13 |  | 100 µM | 108% | +40% |
| 14 |  | 200 µM | 114% | +48% |

*Score of the dermal collagen of the untreated sample (#1) was set to 100%
°Positive control for collagen inhibition (−23% vs. untreated (#1))

As can be retrieved from the results outlined in Table B, the 11β-HSD1 inhibitors according to the present invention counteracted cortisone activity by restoring or even enhancing total collagen in the papillary dermis.

2. Total Dermal Collagen III After UV-Irradiation

Human skin from abdominal plastic surgery classified as "Intermediate" (ITA° angle=42°) was used. The skin samples were cut in pieces of approx. 8×3 mm (0×thickness) and cultured up to day 6 in an air-liquid interface in a perforated ring of stainless steel in contact with a culture medium (modified Williams' E medium, while renewing the culture medium on day 3. Six skin specimens were used for each test sample. Each test sample (4 µl) was topically applied on top of each piece after gentle cleaning of the surface with a cotton pad, which was subsequently covered with a 6 ø mm delivery membrane, this procedure was repeated daily. The samples were irradiated daily with 80% of the Biological effective dose for daylight (i.e. 6 J/cm$^2$) using an adopted BIO-SUN system (Vilber Lourmat). At day 6 twelve skin sections were immunostained with mouse monoclonal anti-collagen III antibody (Sigma cat #c7805). The papillary dermis was selected for the analysis. The evaluation was performed by estimating both color intensity and distribution with IMAGE J (NIH) analysis software. Two slides of each skin sample have been processed by image acquisition and related analysis (i.e. 12 images for each treatment).

TABLE C

| Dermal Collagen III at day 6 | | | | | |
|---|---|---|---|---|---|
| | Test sample | | | Dermal | Increase versus UV |
| # | compound | Conc. (in DMSO) | UV | collagen III* | treatment (#2) |
| 1 | none | 0 µM | N | 100% | — |
| 2 | none° | 0 µM | Y | 80% | — |
| 3 | (IV-a) | 10 µM | Y | 90% | +13% |
| 4 |  | 100 µM | Y | 97% | +21% |
| 5 | (II-a) | 10 µM | Y | 84% | +5% |

TABLE C-continued

Dermal Collagen III at day 6

| # | Test sample compound | Conc. (in DMSO) | UV | Dermal collagen III* | Increase versus UV treatment (#2) |
|---|---|---|---|---|---|
| 6 | | 100 μM | Y | 114% | +43% |
| 7 | (IV-f) | 10 μM | Y | 85% | +6% |
| 8 | | 100 μM | Y | 106% | +33% |

*Score of the dermal collagen III of the non UV treated sample (#1) was set to 100%
°Positive control for UV-damage (−20% vs. untreated (#1))

As can be retrieved from the results outlined in Table C, the 11β-HSD1 inhibitors according to the present invention counteracted UV damage by restoring or even enhancing dermal collagen III in the papillary dermis.

Example 23 Solubility Test

The solubility of selected compounds was tested in the cosmetic oils Cetiol B (INCI name: dibutyl adipate from BASF Personal Care), DUB DIS (INCI name: diisopropyl sebacate from Stearinerie Dubois) and Finsolv EB ((INCI name: ethylhexyl benzoate from Innospec Performance Chemicals).

Preparation of Calibration Curves

Samples of about 1 mg of the compounds to be tested were exactly weighted and dissolved in 90% $MeCN_{(aq)}$ to provide 0.1% (1000 ppm) w/v stock solutions. Aliquots of the stock solutions were diluted with 90% $MeCN_{(aq)}$ to provide 10, 100 and 250 ppm diluted solutions, which were tested by UPLC. The integrals of the analogue peaks detected at λ 216 nm proved to be directly proportional to the sample concentration in the calibration range and were used for the preparation of calibration curves.

Determination of the Solubility from Saturated Mixtures

For each compound to be tested about 20 mg material were weighted in three microcentrifuge tubes and to each tube about 150 mg of one cosmetic oil were added, as reported in Table 5 below.

TABLE 5

Amount of compound and cosmetic oil used in the preparation of the saturated mixtures[a]

| Compound | in Cetiol B | in DUB DIS | in Finsolv EB |
|---|---|---|---|
| IIa | 21.12 mg in 148.82 mg | 20.44 mg in 146.09 mg | 21.15 mg in 156.54 mg |
| IIk | 19.85 mg in 151.04 mg | 20.13 mg in 146.86 mg | 19.80 mg in 152.55 mg |
| IIIb | 23.77 mg in 149.78 mg | 19.18 mg in 148.30 mg | 20.54 mg in 153.06 mg |
| IVc | 21.26 mg in 152.14 mg | 21.02 mg in 146.80 mg | 20.18 mg in 156.81 mg |
| IVf | 20.28 mg in 150.28 mg | 19.66 mg in 146.40 mg | 19.74 mg in 152.51 mg |

[a]The first number refers to amount of compound, the second to the amount of cosmetic oil.

After mixing on a Vortex mixer for 5 min, the respective samples were mixed on a waving platform shaker (20 cycles/min) for 7 days at room temperature (22° C.). After that time, the tubes were centrifuged for 5 min at 12000 rpm, 10 μL samples of the supernatant were diluted to 1.00 mL with MeOH, 100 μL of these solutions were diluted to 1.00 mL with 90% $MeCN_{(aq)}$ and subsequently analyzed by UPLC. The compound concentration in each solution was calculated using the respective calibration curve. From the compound concentration in the diluted solutions the concentrations of the respective parent mixtures was calculated accordingly. The results are outlined in Table 6 below.

TABLE 6

Solubility in cosmetic oils

| Compound | Cetiol B | DUB DIS | Finsolv EB |
|---|---|---|---|
| IIa[a] | 13.2%[b] | 10.6%[b] | 10.2%[b] |
| IIk | 3.0% | 2.4% | 3.4% |
| IIIb | 10.0% | 4.3% | 2.6% |
| IVc | 3.3% | 2.6% | 4.0% |
| IVf | 10.6%[b] | 10.2%[b] | 10.3%[b] |

[a]Mixture of two diastereomers (4:1).
[b]Mixture not saturated, therefore solubility might be even higher.

Determination of the Solubility of IIe and IIh

Precisely weighted amounts of the respective compounds (see Tables 7 and 8) were weighted into 2 mL clear glass vials to which 0.50-0.60 mL of either Cetiol B or DUB DIS was then added. After preliminary mixing on a Vortex mixer for 1 min, the probes were mixed on a waving platform shaker for 3 days at room temperature. After that time, solutions were added with further precisely weighted amounts of the same compound, whereas suspensions were added with small amounts of the same cosmetic oil. This procedure was repeated until suspensions became clear or solutions became saturated. In case the difference between the concentration of the most concentrated clear solution and of the most diluted suspension was larger than 7%, one further intermediate concentration value was tested.

TABLE 7

Solubility ranges obtained in Cetiol B

| Compound | Amount | Most diluted saturated solution | Most concentrated clear solution | Solubility in Cetiol B ($S_{CB}$) |
|---|---|---|---|---|
| IIe | 100 mg | 0.90 mL | 0.92 mL | 10.8% < $S_{CB}$ < 11.2% |
| IIh | 263 mg | 0.54 mL | 0.55 mL | 47.2% < $S_{CB}$ < 49.2% |

TABLE 8

Solubility ranges obtained in in DUB DIS

| Compound | Amount | Most diluted saturated solution | Most concentrated clear solution | Solubility in DUB DIS ($S_{DD}$) |
|---|---|---|---|---|
| IIe | 42 mg | 0.50 mL | 0.52 mL | 8.2% < $S_{DD}$ < 8.5% |
| IIh | 201 mg | 0.52 mL | 0.54 mL | 37.0% < $S_{DD}$ < 38.9% |

As can be retrieved from table 7 and 8, the compound according to the present invention exhibit a high solubility in the cosmetic oils Cetiol B and Dub Dis.

Example 24 Cosmetic Composition

Table 9 outlines exemplary O/W emulsions, wherein one compound selected from the group of II(a-k) [Table 1], III(a-c) [Table 2], and IV(a-g) [Table 3] is incorporated in the indicated amount.

Example 25 Microbiological Challenge Test 500 mg [1,1'-Biphenyl]-3-yl(azepan-1-yl)methanone (IV-f) was added separately to either 250 g ZEMEA (INCI: Propanediol), 250 mg Myritol (INCI: Caprylic/Capric Triglyceride), or 250 g Cetiol OE (INCI: Dicaprylyl Ether). Afterwards the respective mixtures were stirred at room temperature with magnetic stirrer until dissolved. The solutions were then tested according to European Pharmaco-

TABLE 9

| Exemplary O/W emulsion | | | | | | | | |
|---|---|---|---|---|---|---|---|---|
| O/W Emulsions | 1 | 2 | 3 | 4 | 5 | 6 | 7 | 8 |
| Glyceryl Stearate | 2.5 | 2 | 1.2 | 1 | | | 1 | 1 |
| PEG-40 Stearate | 1 | | | | | | | |
| PEG-100 Stearate | | 2.5 | | | | | | 1 |
| Ceteareth-20 | | | | | 1 | | | |
| Glyceryl Stearate Citrate | | | | | | 0.5 | | |
| Potassium Cetyl Phosphate | | | | | | | 3 | 1.5 |
| Stearic Acid | | | 2.5 | 3 | | | | |
| Cetearyl Alcohol | 4 | | | 2 | | | 2 | |
| Stearyl Alcohol | | 2 | 1 | | | | | |
| Cetyl Alcohol | | | 1 | 1 | | | | 0.5 |
| Acrylates/$C_{10-30}$ Alkyl Acrylate Crosspolymer | | | | 0.2 | 0.2 | 0.4 | 0.2 | |
| Carbomer | 0.1 | | 0.2 | | | | | |
| Xanthan Gum | | 0.3 | | | | | | 0.3 |
| $C_{12-15}$Alkyl Benzoate | 5 | | | 2 | 5 | 5 | 10 | 5 |
| Petrolatum | 5 | | 3 | | | | | |
| Butylene Glycol Dicaprylate/Dicaprate | | 4 | 2 | | 9 | | | 9 |
| Hydrogenated Polydecene | | | 3 | | 2 | | | 2 |
| Caprylic/Capric Triglyceride | 1 | 3 | | 5 | | 5 | 5 | |
| Cyclomethicone | | 5 | 2 | | | 10 | | |
| Methylpropanediol | 2 | | | | 3 | | | 3 |
| Glycerine | 4 | 7 | 3 | 4 | 3 | | 5 | 3 |
| Glyceryl Glucoside | 3.5 | 3 | 1 | 1 | 2 | | | 2 |
| Alcohol denat. | 1 | 3 | 0.5 | 10 | 4 | 8 | | 4 |
| Butylene Glycol | | | 3 | | | | | |
| Ascorbylglucoside | | 0.5 | | 1.0 | | 1.5 | | 0.1 |
| Ubiquinone (Coenzyme 10) | 0.1 | | 0.05 | | | | 0.01 | |
| Hyaluronic acid | | | | | 0.2 | | | |
| Bisabolol | 0.5 | | | | | | 0.2 | |
| Isotridecylsalicylate | | | 1 | 3 | 5 | 2 | 3 | 5 |
| Compound selected from the group of II(a-k), II(a-c), and IV(a-g) | 0.001 | 0.25 | 0.0001 | 0.05 | 0.1 | 0.0003 | 0.03 | 0.002 |
| Dibutyl Adipate | 1.5 | 3 | | | | | | |
| Diisopropyl sebacate | | | 1 | 1 | 2 | 3 | | |
| Ethylhexyl Benzoate | | | | | | 0.75 | 1.5 | 1 |
| Titanium Dioxide (PARSOL TX) | | | 0.5 | 2 | | | | |
| Methylene Bis-Benzotriazolyl Tetramethylbutylphenol | | | 0.5 | 4 | | 6 | | 2 |
| Ethylhexyl methoxycinnamate | | | | | 2 | | | |
| Phenylbenzimidazole Sulfonic Acid | | | | 2 | | 2 | 2 | |
| Butyl Methoxydibenzoylmethane | | 1 | | 2 | 2 | 3 | 3 | 3 |
| Methylbenzylidene Camphor | | | | | 2 | 3 | | |
| Octocrylene | | 5 | | | | 2 | 10 | |
| Polysilicone-15 | | | | 2 | | 3 | | |
| Ethylhexyl Salicylate | | | | | 5 | | | |
| Homosalate | | | | 4 | | 2 | | |
| Bis-Ethylhexyloxyphenol Methoxyphenyltriazine | | 1.5 | | | | | | 2 |
| Silica | 1 | | 2.5 | | | 0.5 | | |
| Silica & Methicone | | 4 | | 1 | 2.5 | | | |
| Methyl Methacrylate Crosspolymer | | | | 1 | | | 2 | |
| Disodium EDTA | 0.1 | | | | | 0.5 | | |
| Fragrance, Preservatives | | | | q.s. | | | | |
| Sodium Hydroxide | | | | q.s. | | | | |
| Water | | | | Ad 100 | | | | |

The invention claimed is:

1. A cosmetic composition comprising:
(i) a compound of formula (I):

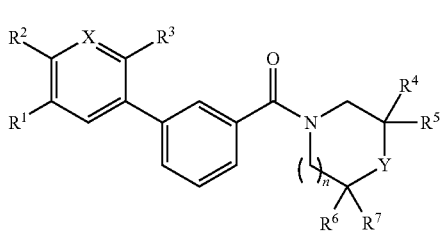

wherein X is CH or N,
Y is CHR⁸ or O,
n is 0, 1 or 2,
R¹, R² and R³ are independently of each other selected from the group consisting of H, OH, a halogen atom, a carbamoyl group and $C_1$-$C_6$alkyl group, and
R⁴, R⁵, R⁶, R⁷ and R⁸ are independently of each other H or a $C_1$-$C_6$alkyl group, and
(ii) a cosmetically acceptable carrier.

2. The cosmetic composition according to claim 1, wherein the compound of formula (I) is present in an amount within a range of about 0.00001 to 0.5 wt.-%, based on total weight of the cosmetic composition.

3. The cosmetic composition according to claim 1, wherein the compound of formula (I) is a compound of formula (Ia):

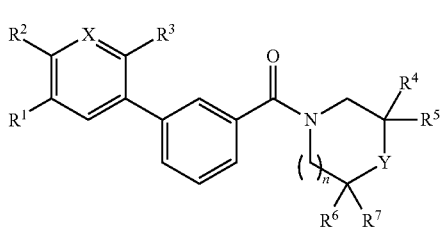

wherein X is CH or N,
Y is CHR⁸ or O,
n is 1 or 2,
R¹, R² and R³ are independently of each other selected from the group consisting of H, OH, a halogen atom, a carbamoyl group and a $C_1$-$C_6$alkyl group, and
R⁴, R⁵, R⁶, R⁷ and R⁸ are independently of each other H or a $C_1$-$C_6$alkyl group,
with the proviso that if
(i) n is 1 and Y is CHR⁸, then at least one of R⁴, R⁵ or R⁸ is a $C_{1-6}$alkyl group; or
(ii) n is 2, Y is CHR⁸, X is CH and R¹, R³, R⁴, R⁵, R⁶, R⁷ and R⁸ are H, then R² is not F; or
(iii) n is 1 and Y is O, then R² and at least one of R⁴ or R⁵ are a $C_1$-$C_6$alkyl group.

4. The cosmetic composition according to claim 1, wherein the compound of formula (I) contains only one residue selected from the group consisting of OH, a halogen atom and a carbamoyl group.

5. The cosmetic composition according to claim 1, wherein the $C_1$-$C_6$alkyl group is an unbranched $C_1$-$C_3$alkyl group.

6. The cosmetic composition according to claim 1, wherein the halogen atom is F or Cl.

7. The cosmetic composition according to claim 1, wherein the compound of formula (I) is a compound of formula (II):

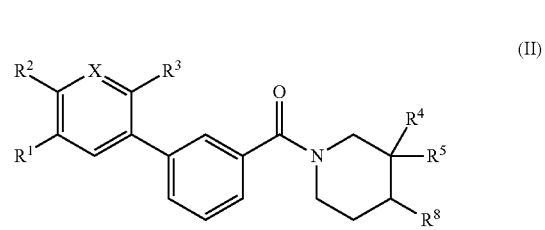

wherein X is CH or N,
R¹, R² and R³ are independently of each other selected from the group consisting of H, OH, a halogen atom, a carbamoyl group and a $C_1$-$C_6$alkyl group, and
R⁴, R⁵ and R⁸ are independently of each other H or a $C_1$-$C_6$alkyl group,
with the proviso that at least one of R⁴, R⁵ and R⁸ is a $C_{1-6}$alkyl group.

8. The cosmetic composition according claim 7, wherein the compound of formula (II) is a compound selected from the group consisting of (4-methylpiperidin-1-yl) (3-(6-methylpyridin-3-yl)phenyl)methanone (II-a), (4'-hydroxy-[1,1'-biphenyl]-3-yl)(4-methylpiperidin-1-yl)methanone (II-b), (4'-fluoro-[1,1'-biphenyl]-3-yl)(4-methylpiperidin-1-yl) methanone (III-c), (3'-fluoro-4'-methyl-[1,1'-biphenyl]-3-yl) (4-methylpiperidin-1-yl)methanone (III-d), (2'-chloro-[1,1'-biphenyl]-3-yl)(4-methylpiperidin-1-yl)methanone (II-e), (4'-methyl-[1,1'-biphenyl]-3-yl)(4-methylpiperidin-1-yl) methanone (II-f), (4'-chloro-[1,1'-biphenyl]-3-yl)(4-methylpiperidin-1-yl)methanone (II-g), (3,3-dimethylpiperidin-1-yl)(3'-fluoro-4'-methyl-[1,1'-biphenyl]-3-yl)methanone (II-h), 3'-(4-methylpiperidine-1-carbonyl)-[1,1'-biphenyl]-4-carboxamide (II-i), (3'-hydroxy-[1,1'-biphenyl]-3-yl)(4-methylpiperidin-1-yl)methanone (II-j), and 3'-(4-methylpiperidine-1-carbonyl)-[1,1'-biphenyl]-3-carboxamide (II-k).

9. The cosmetic composition according to claim 1, wherein the compound of formula (I) is a compound of formula (III):

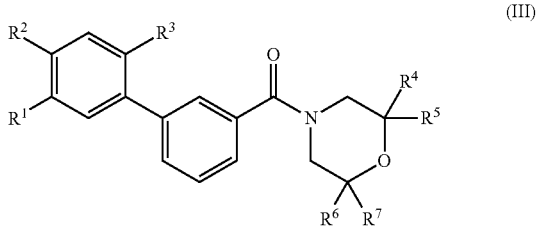

wherein R¹ and R³ are independently of each other selected from the group consisting of H, OH, a halogen atom and a $C_1$-$C_6$alkyl group, $R^2$ is a $C_1$-$C_6$ alkyl group, and
$R^4$, $R^5$, $R^6$ and $R^7$ are independently of each H or a $C_1$-$C_6$ alkyl group, with the proviso that at least one of $R^4$ or $R^5$ are a $C_1$-$C_6$ alkyl group.

10. The cosmetic composition according to claim 9, wherein the compound of formula (III) is a compound selected from the group consisting of (2,2-dimethylmorpholino) (3'-fluoro-4'-methyl-[1,1'-biphenyl]-3-yl)methanone (III-a), (2,6-dimethylmorpholino) (3'-fluoro-4'-methyl-[1,1'-biphenyl]-3-yl)methanone (III-b) and (2,6-dimethylmorpholino) (4'-methyl-[1,1'-biphenyl]-3-yl)methanone (III-c).

11. The cosmetic composition according to claim 1, wherein the compound of formula (I) is a compound of formula (IV):

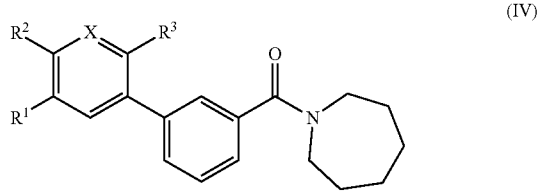

(IV)

wherein X is CH or N, and
$R^1$, $R^2$ and $R^3$ are independently of each other selected from the group consisting of H, OH, a halogen atom and a $C_1$-$C_6$ alkyl group,
with the proviso that if X is CH and $R^1$ and $R^3$ are H, then $R^2$ is not a F atom.

12. The cosmetic composition or the compound according claim 11, wherein the compound of formula (IV) is a compound selected from the group consisting of azepan-1-yl(3'-fluoro-4'-methyl-[1,1'-biphenyl]-3-yl)methanone (IV-a), azepan-1-yl(4'-chloro-[1,1'-biphenyl]-3-yl)methanone (IV-b), azepan-1-yl(4'-methyl-[1,1'-biphenyl]-3-yl)methanone (IV-c), azepan-1-yl(4'-hydroxy-[1,1'-biphenyl]-3-yl)methanone (IV-d), azepan-1-yl(3-(6-methylpyridin-3-yl)phenyl)methanone (IV-e), [1,1'-biphenyl]-3-yl(azepan-1-yl)methanone (IV-f), and azepan-1-yl(3',4'-dimethyl-[1,1'-biphenyl]-3-yl)methanone (IV-g).

13. The cosmetic composition according to claim 1, wherein n is 1 or 2.

14. The cosmetic composition according to claim 2, wherein the compound of formula (I) is present in an amount with a range of 0.0001 to 0.25 wt.-%, based on the total weight of the cosmetic composition.

15. The cosmetic composition according to claim 2, wherein the compound of formula (I) is present in an amount with a range of 0.0001 to 0.1 wt.-%, based on the total weight of the cosmetic composition.

16. The cosmetic composition according to claim 5, wherein the $C_1$-$C_6$ alkyl group is a $C_1$-$C_2$ alkyl group.

17. The cosmetic composition according to claim 5, wherein the $C_1$-$C_6$ alkyl group is a methyl group.

18. A method to smoothen wrinkles and fine lines and/or to decrease volume and depth of wrinkles and fine lines, wherein the method comprises the step of applying to an area of skin affected by wrinkles and fine lines an effective amount of the cosmetic composition according to claim 1.

19. The method according to claim 18, wherein the cosmetic composition is applied to the area of skin in an amount of between 0.1 to 3 mg/cm² of skin.

20. A method for the treatment of (photo)age-induced skin structure and function defects which comprises applying to an area of skin affected by (photo)age-induced skin structure and function defects an effective amount of the cosmetic composition according to claim 1.

21. The method according to claim 4, wherein the cosmetic composition is applied to the area of skin in an amount of between 0.1 to 3 mg/cm² of skin.

* * * * *